US011385186B2

(12) United States Patent
Oyama et al.

(10) Patent No.: US 11,385,186 B2
(45) Date of Patent: Jul. 12, 2022

(54) INSPECTION APPARATUS USING TH_BAND

(71) Applicant: LAUREL PRECISION MACHINES CO., LTD., Osaka (JP)

(72) Inventors: Yutaka Oyama, Sendai (JP); Kouichi Goi, Tokyo (JP)

(73) Assignee: LAUREL PRECISION MACHINES CO., LTD., Osaka (JP)

(*) Notice: Subject to any disclaimer, the term of this patent is extended or adjusted under 35 U.S.C. 154(b) by 327 days.

(21) Appl. No.: 15/518,981

(22) PCT Filed: Oct. 9, 2015

(86) PCT No.: PCT/JP2015/078856
§ 371 (c)(1),
(2) Date: Apr. 13, 2017

(87) PCT Pub. No.: WO2016/060094
PCT Pub. Date: Apr. 21, 2016

(65) Prior Publication Data
US 2017/0234807 A1  Aug. 17, 2017

(30) Foreign Application Priority Data
Oct. 14, 2014 (JP) .............................. JP2014-210329

(51) Int. Cl.
*G01N 21/89* (2006.01)
*G01N 21/3581* (2014.01)
(Continued)

(52) U.S. Cl.
CPC ..... *G01N 21/8914* (2013.01); *G01N 21/3581* (2013.01); *G01N 21/892* (2013.01);
(Continued)

(58) Field of Classification Search
CPC .......... G01N 21/8914; G01N 21/3581; G01N 21/892; G01N 21/94; G01N 33/346
(Continued)

(56) References Cited

U.S. PATENT DOCUMENTS 7,015,444 B2 * 3/2006 Kawano ............... G02B 21/004
250/201.3
9,893,423 B2 * 2/2018 Debray ................... H01Q 7/00
2005/0141759 A1 6/2005 Mori et al.

FOREIGN PATENT DOCUMENTS

JP    5-79996 A     3/1993
JP    11-173997 A   7/1999
(Continued)

OTHER PUBLICATIONS

International Search Report dated Jan. 19, 2016, issued in counterpart application No. PCT/JP2015/078856. (2 pages).

Primary Examiner — David P Porta
Assistant Examiner — Carolyn Fin
(74) Attorney, Agent, or Firm — WHDA, LLP

(57) ABSTRACT

An inspection device of the present invention includes: THz wave irradiation unit for irradiating a specimen with THz waves; a THz wave sensing unit for detecting transmitted waves or reflected waves of the THz waves emitted to the specimen; and an information processing unit for acquiring intensity distribution of the transmitted waves of the reflected waves of the specimen from the intensity data of the transmitted waves or the reflected waves of the specimen irradiated with the THz waves, wherein the information processing unit acquires 2-dimensional intensity distribution of the transmitted waves or reflected waves, and detects whether a foreign matter is adhering to the specimen by comparing the intensity distribution obtained when the specimen without attachment of the foreign matter is detected and the intensity distribution obtained when the (Continued)

specimen is detected at the time of inspection. The specimen is a sheet of paper, for example.

13 Claims, 27 Drawing Sheets

(51) Int. Cl.
  *G01N 21/892* (2006.01)
  *G01N 22/00* (2006.01)
  *G01N 22/02* (2006.01)
  *G07D 7/12* (2016.01)
  *G07D 7/121* (2016.01)
  *G07D 7/189* (2016.01)
  *G01N 21/94* (2006.01)
  *G01N 33/34* (2006.01)

(52) U.S. Cl.
  CPC ............. *G01N 21/94* (2013.01); *G01N 22/00* (2013.01); *G01N 22/02* (2013.01); *G01N 33/346* (2013.01); *G07D 7/12* (2013.01); *G07D 7/121* (2013.01); *G07D 7/189* (2017.05); *G01N 2021/8917* (2013.01)

(58) Field of Classification Search
  USPC ...................................... 250/338.1
  See application file for complete search history.

(56) References Cited

FOREIGN PATENT DOCUMENTS

| | | |
|---|---|---|
| JP | 2000-259885 A | 9/2000 |
| JP | 2005-174069 A | 6/2005 |
| JP | 2007-72885 A | 3/2007 |
| JP | 2009-300279 A | 12/2009 |
| JP | 2011-34173 A | 2/2011 |
| JP | 2011-220901 A | 11/2011 |
| JP | 2013-228329 A | 11/2013 |

* cited by examiner

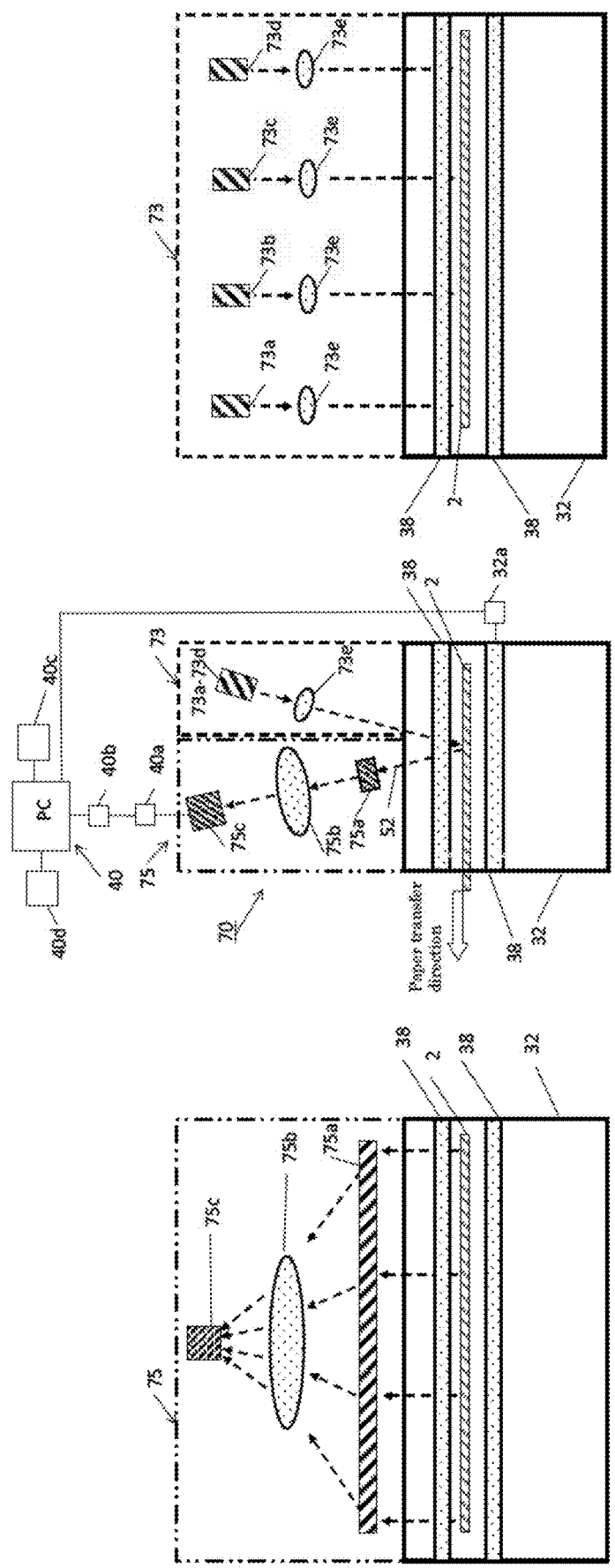

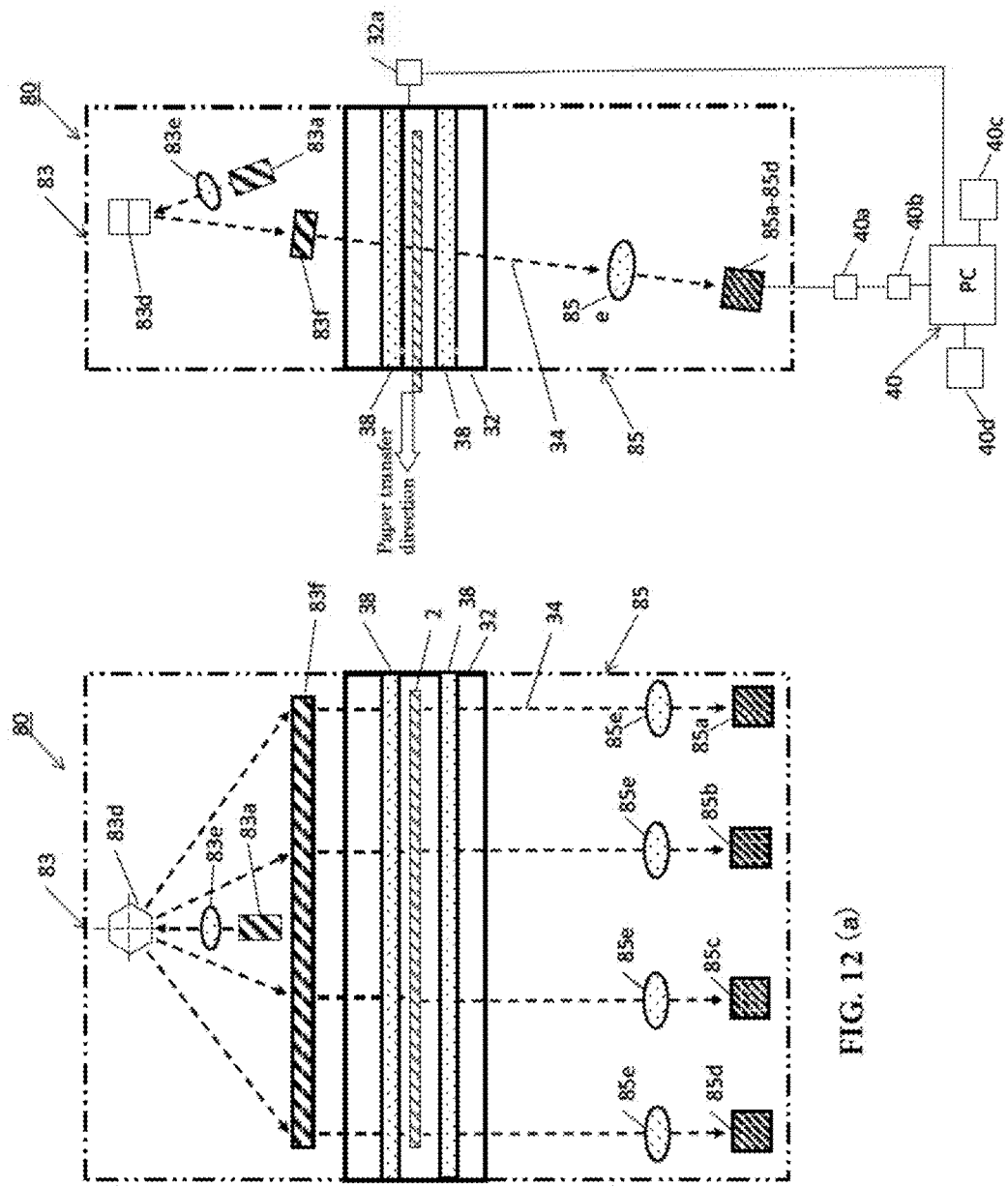

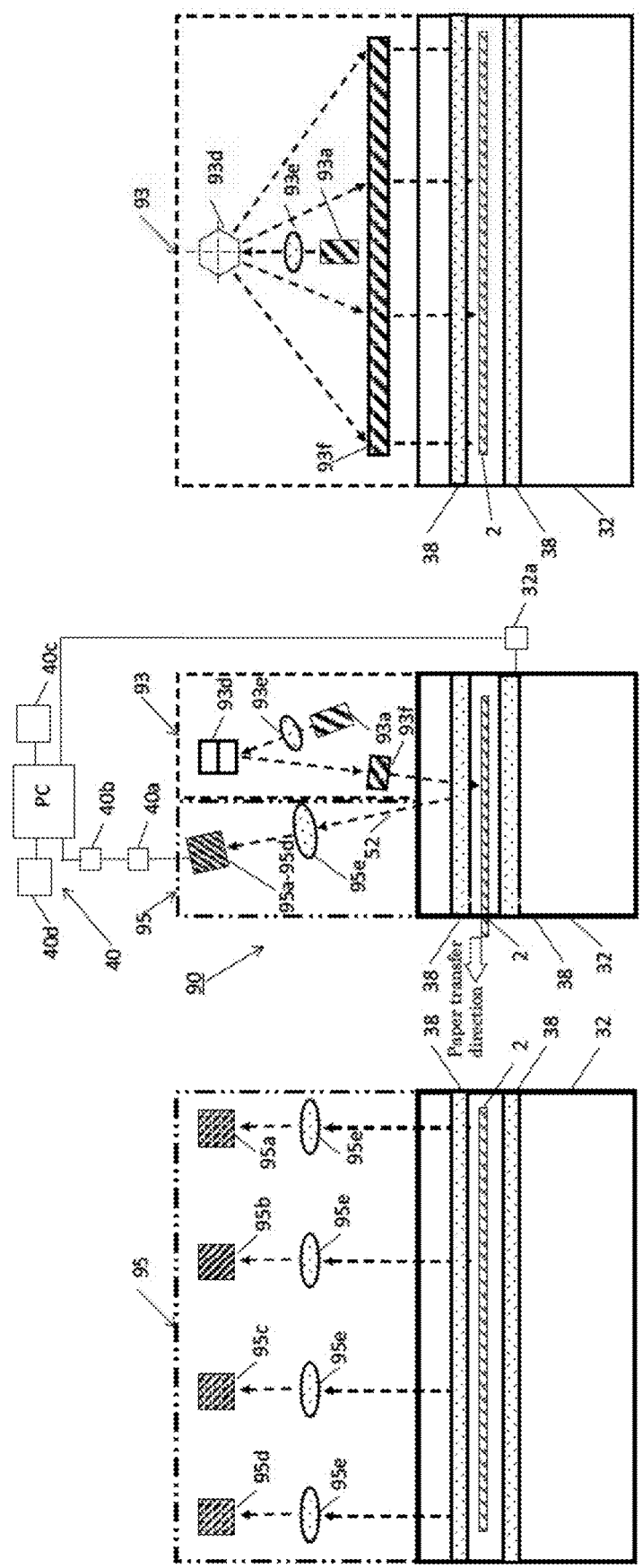

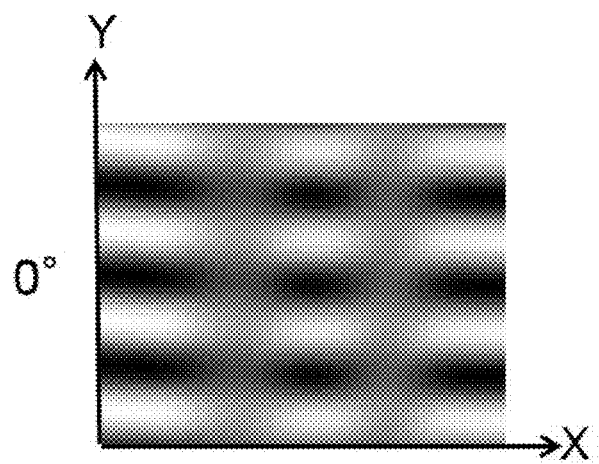
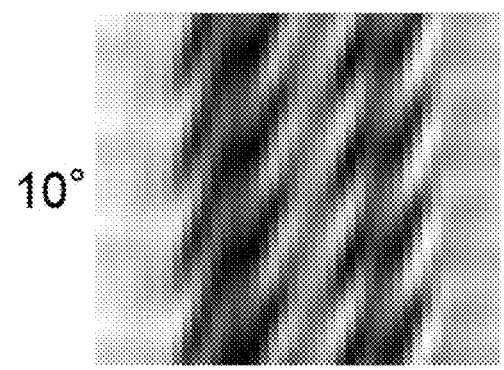
FIG. 19 (a)                FIG. 19 (b)
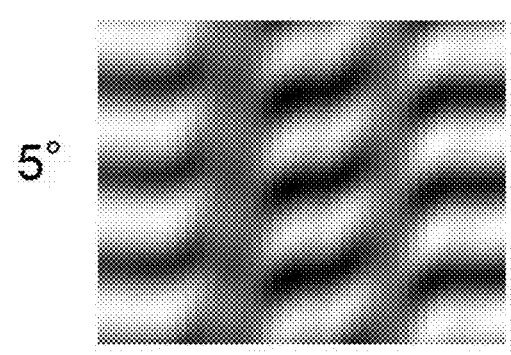
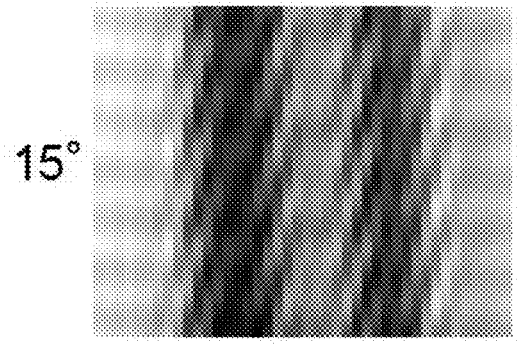
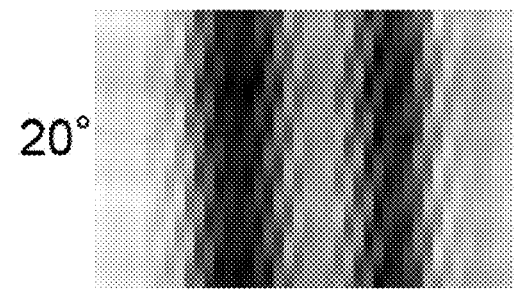
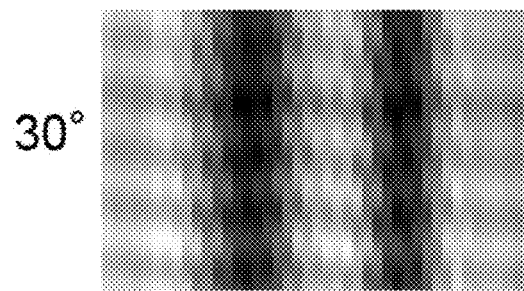
FIG. 19 (c)                FIG. 19 (d)

FIG. 22
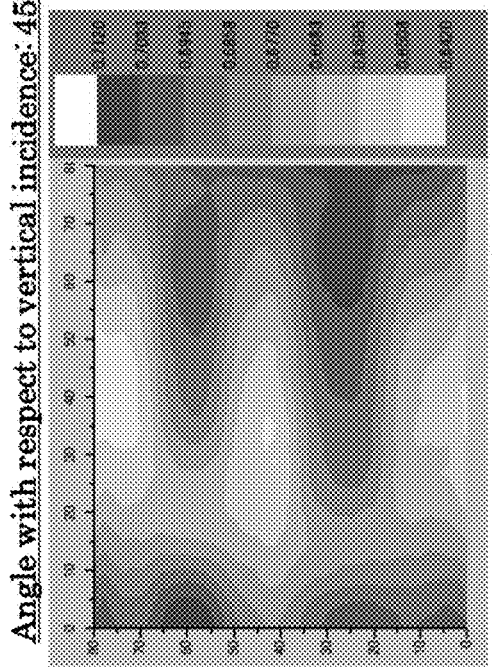
Tape on both faces of copy paper
Number of contour levels: 12
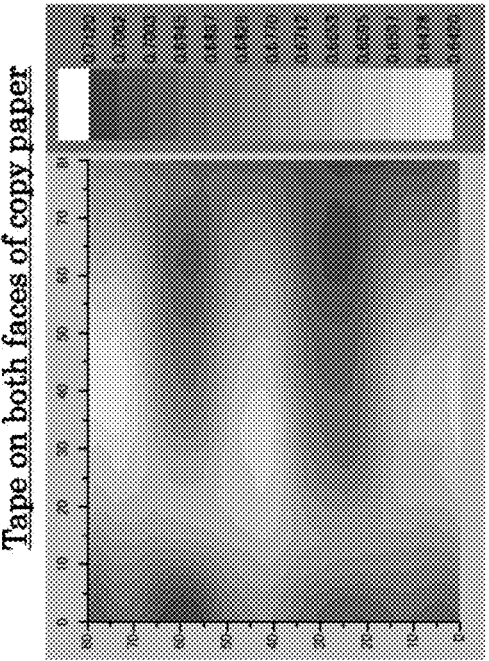
Angle with respect to vertical incidence: 45°
Number of contour levels: 8
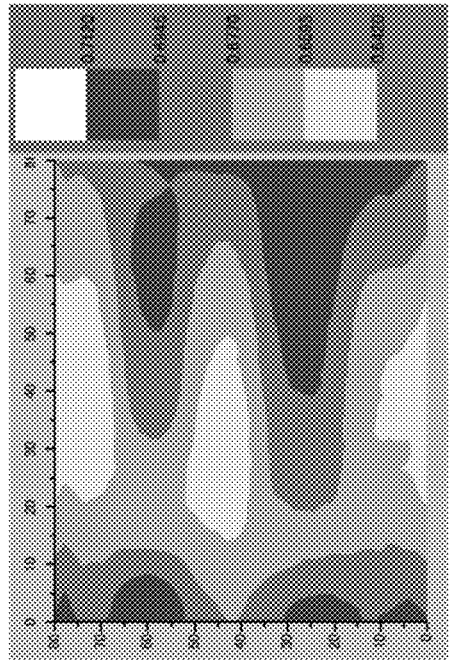
Number of contour levels: 4

FIG. 23
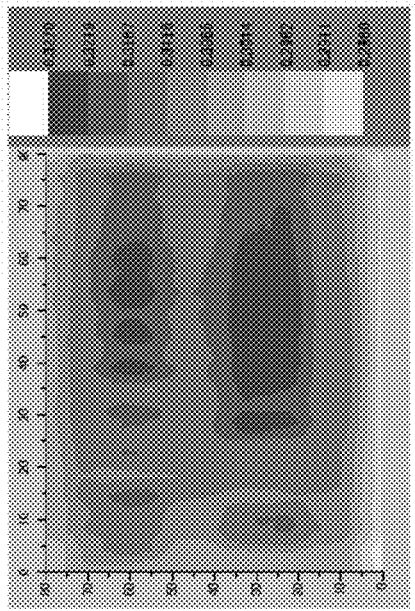
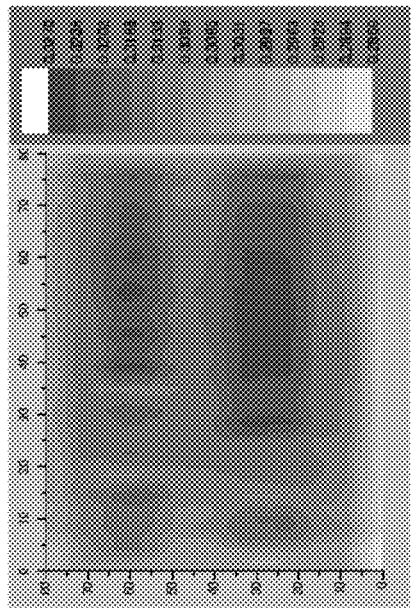
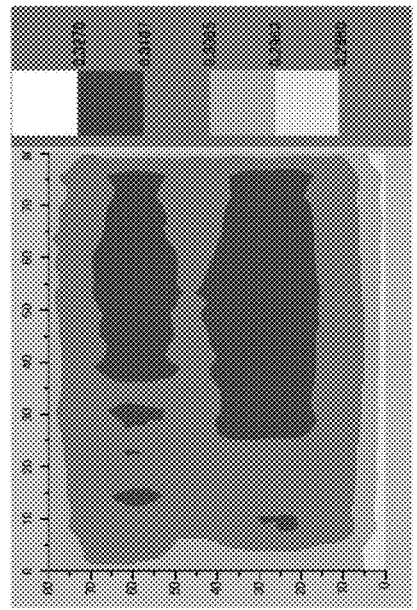

FIG. 24
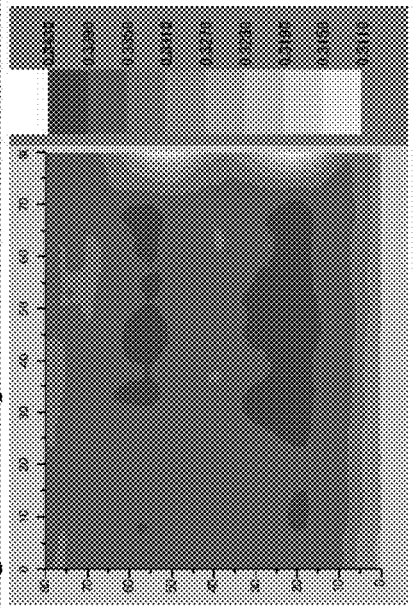
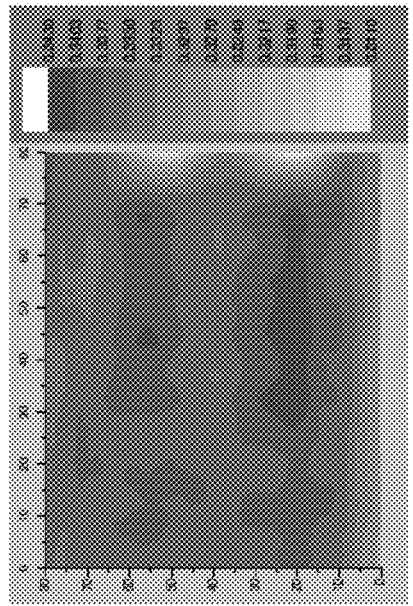
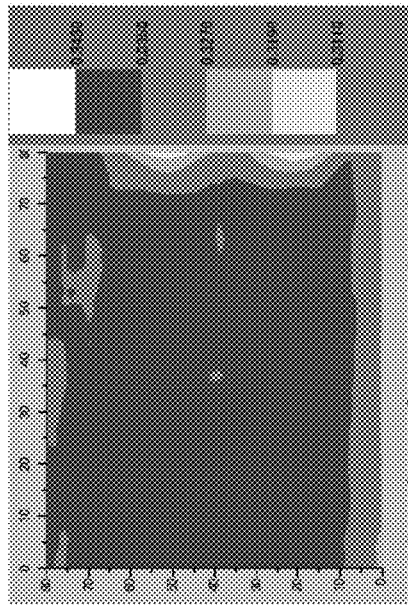

FIG. 25
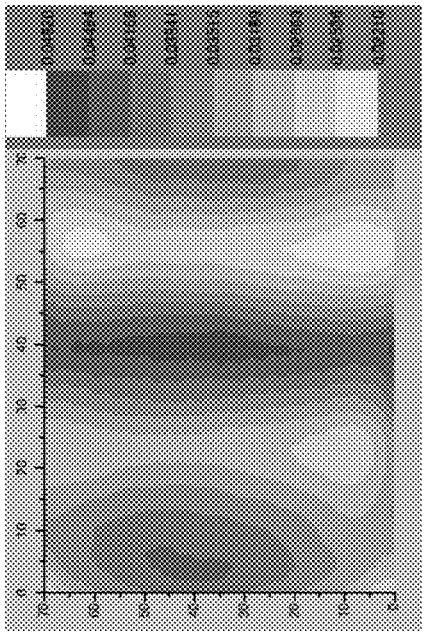
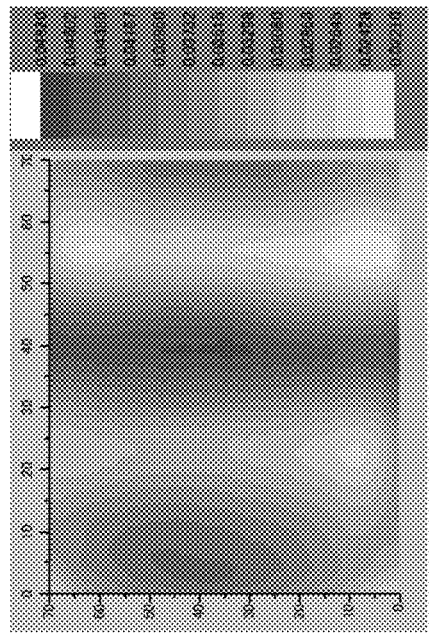
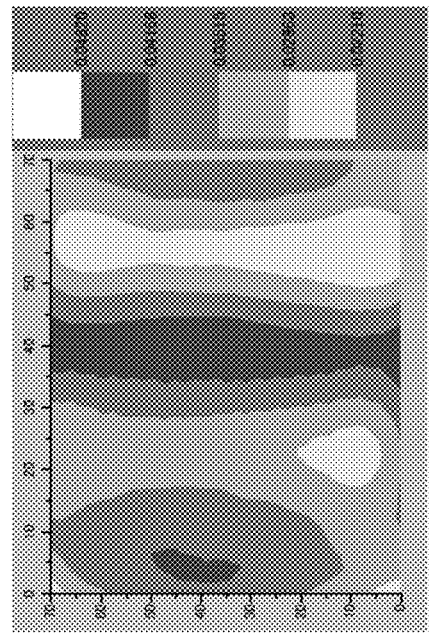

FIG. 26
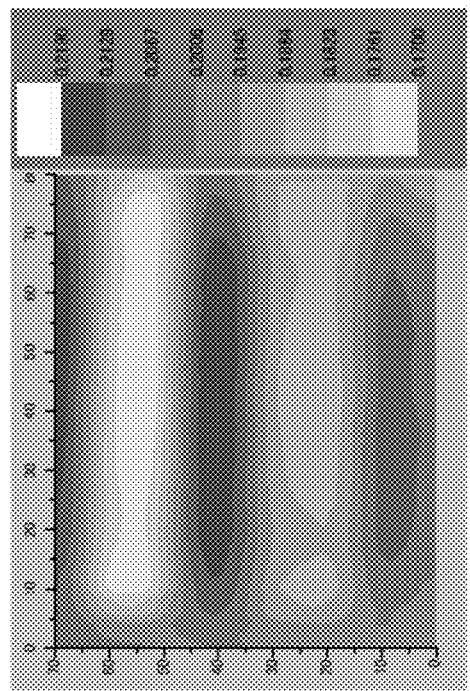
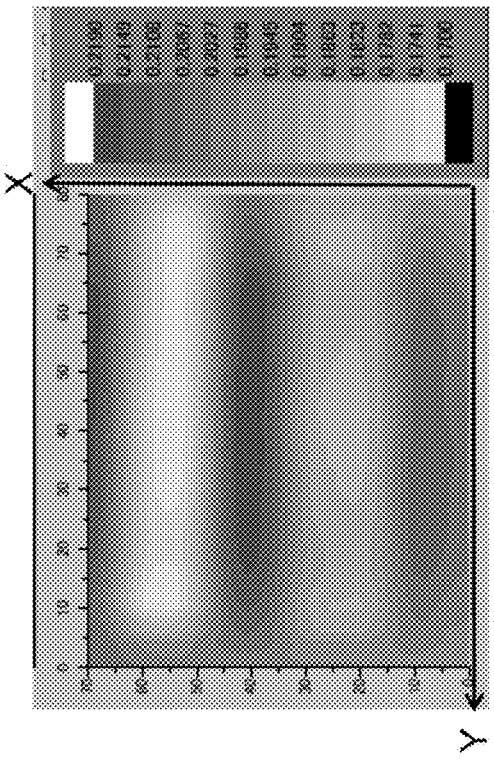
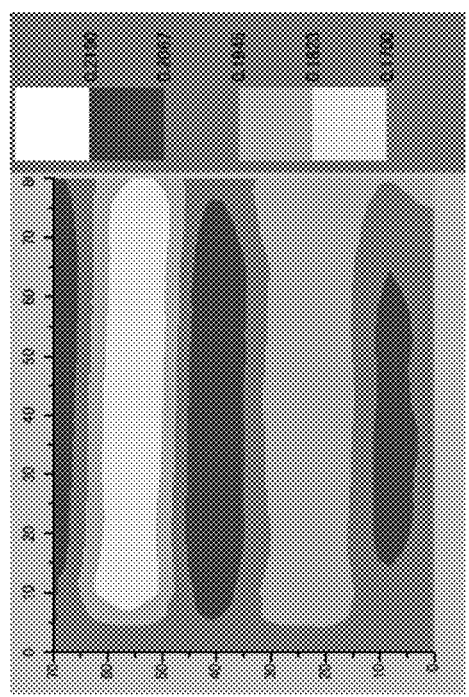

INSPECTION APPARATUS USING TH$_z$ BAND

TECHNICAL FIELD

The present invention relates to an inspection device using THz band, the inspection device using the THz band capable of detecting foreign matter adhering to a specimen easily, in particular.

BACKGROUND ART

Since sheets of paper such as paper money are folded repetitively while being used, the sheets may be broken partially while being used for a long time. In such cases, users may repair the broken part by attaching a tape, etc. to the broken part. Also, repairing the broken part by attaching the tape, etc. by cut and paste may raise a concern of alteration. Such sheets of paper are no longer regarded as normal.

To distinguish a sheet of paper to which the tape has been attached from normal sheets, whether the tape is attached or not has conventionally been assessed by mechanically measuring slight difference in thickness due to attachment of the tape by contact. However, if the attached tape is extremely thin, there is a concern that detection might fail, or a mechanical contact might damage the sheet.

A method for inspecting objects using the THz band has recently been developed rapidly. The THz band, which is also called THz waves, is a frequency band whose wavelength ranges from 10 mm to 15 μm, namely from 30 GHz (1 GHz equals to $10^9$ Hz) to 12 THz, and has a property of conventional radio waves and light at the same time. The THz waves are also called terahertz light or terahertz electromagnetic waves.

Patent Literature 1 discloses an inspection device for detecting the thickness of a sheet of paper and foreign matter adhering to the sheet of paper by irradiating the sheet of paper with THz waves, and detecting the intensity of interference due to phase difference between the reflected waves of the THz waves from the front face of the sheet of paper and the reflected waves of the THz waves from the back face of the sheet of paper.

With the inspection device disclosed in Patent Literature 1, a laser with fixed wavelength and a laser with variable wavelength are made to enter into a photoconductive antenna for emission (photoconduction), which generates THz waves equivalent to the difference in frequencies between these lasers.

Patent Literature 2 discloses a device for irradiating a sheet of paper with THz waves and finding the refraction index of the sheet of paper based on the intensity of interference due to phase difference between reflected waves of the THz waves from the front face of the sheet of paper and the reflected waves of the THz waves from the back face of the sheet of paper, or on amplitude reflectance.

With the inspection device disclosed in Patent Literature 2, the first and the second DFB lasers for communication in 1.5 μm band are mixed via an optical fiber or a fiber coupler and made to enter into the first and the second transmitters, and the first and the second transmitters generate THz waves equivalent to the frequency difference between the first and the second DFB lasers for communication. The first and the second transmitters are made of uni travelling carrier-photo diode (UTC-PD), for example.

CITATION LIST

Patent Literature

Patent Literature 1: JP 2009-300279 A
Patent Literature 2: JP 2011-34173 A

SUMMARY OF INVENTION

Technical Problem

The inspection device used for conventional measurement using THz waves is complicated, and the judgment of whether the tape is adhering to the sheet of paper has yet to be achieved.

A purpose of the present invention is to provide an inspection device using THz band capable of performing a non-contact detection of foreign matter adhering to the specimen at high speed, highly efficiently, and at the same time at low cost.

Solution to Problem

An inspection device of the present invention includes: a THz wave irradiation unit for irradiating a specimen with THz waves; a THz wave sensing unit for detecting transmitted waves or reflected waves of the THz waves emitted to the specimen; and an information processing unit for acquiring an intensity distribution of the transmitted waves or the reflected waves of the specimen based on the intensity data of the transmitted waves or reflected waves of the specimen irradiated with the THz waves, wherein the information processing unit acquires 2-dimensional intensity distribution of the transmitted waves or the reflected waves, and detects whether a foreign matter is adhering to the specimen at the time of inspection by comparing the intensity distribution obtained when the specimen without attachment of the foreign matter is detected and the intensity distribution obtained when the specimen is detected during inspection.

In the above configuration, the information processing unit may detect the foreign matter adhering to the specimen from the change in intensity by the lens effect based on the difference between the refractive index of the foreign matter and the refractive index of the specimen without attachment of foreign matter.

Another inspection device of the present invention includes: a paper transfer unit for transferring a sheet of paper; a THz wave irradiation unit for emitting THz waves in a direction orthogonal to the transferring direction of the paper transfer unit; a THz wave sensing unit for detecting transmitted or reflected waves of the THz waves emitted to the sheet of paper; and an information processing unit for acquiring intensity distribution of the transmitted waves or reflected waves of the sheet of paper from the intensity data of the transmitted waves or the reflected waves of the sheet of paper irradiated with the THz waves in a direction orthogonal to the transfer direction, wherein the information processing unit acquires the 2-dimensional intensity distribution of the transmitted waves or the reflected waves, and detects whether a foreign matter is adhering to the specimen at the time of inspection by comparing the intensity distribution obtained when the specimen without attachment of the foreign matter is detected and the intensity distribution obtained when the specimen is detected during inspection.

In the above configuration, the information processing unit may detect the foreign matter adhering to the sheet of paper from the change in intensity by the lens effect based on the difference between the refractive index of the foreign matter and the refractive index of the specimen without attachment of foreign matter.

In the above configuration, the THz wave irradiation unit preferably includes: a THz wave oscillator; a light-collecting optical component for scanning the THz waves emitted from the THz wave oscillator; and a scanning element. The scanning element is preferably any one of galvanometer mirror, polygon-mirror, and digital-mirror elements.

The THz wave irradiation unit preferably includes a plurality of THz wave oscillators and a plurality of optical components.

The THz wave sensing unit preferably includes a THz wave detector and a light-collecting optical component for collecting transmitted waves or reflected waves of the THz waves emitted to the sheet of paper.

The light-collecting optical component is preferably selected from Fresnel lens, convex lens, concave lens, and a mirror.

The THz wave sensing unit preferably includes a plurality of THz wave detectors, and a plurality of optical components.

The information processing unit is preferably equipped with a function for 2-dimensionally displaying the change in intensity based on lens effect in different gradations.

The foreign matter is a resin film such as adhesion tape, for example.

To a top face or a bottom face of the specimen or the sheet of paper, resin or glass that allows THz waves to pass through may be disposed.

The THz wave irradiation unit is preferably equipped with a multi-frequency THz wave oscillator.

Direction of polarization of the THz waves emitted by the THz wave irradiation unit to the specimen or the sheet of paper, or of the THz waves coming into the THz wave detectors may be controlled.

Advantageous Effects of Invention

According to the present invention, the non-contact inspection of specimens such as the tape adhering to the sheet of paper, the paper money for example, can be performed clearly, at high speed, and without damage to the sheet of paper, which occurs frequently with conventional mechanical strong contact method.

BRIEF DESCRIPTION OF DRAWINGS

FIG. 11 (a) to FIG. 11 (c) are drawings describing an inspection device according to modification 1 of the third embodiment, where FIG. 11 (a) is a front view. FIG. 11(b) is a right-side view, and FIG. 11 (c) is a rear view.

FIG. 12 (a) and FIG. 12 (b) are drawings describing an inspection device according to modification 2 of the third embodiment of the present invention, where FIG. 12 (a) is a front view, and FIG. 12 (h) is a right-side view.

FIG. 13 (a) to FIG. 13 (c) are drawings describing an inspection device according to modification 3 of the third embodiment of the present invention, where FIG. 13 (a) is a front view, FIG. 13 (b) is a right-side view, and FIG. 13 (c) is a rear view.

FIG. 19 (a) to FIG. 19 (d) are charts showing 2-dimensional intensity of transmitted waves obtained by attaching a mending tape and a cellophane tape in parallel to copy paper and changing the angle of incidence of the 90 GHz transmitted waves, where FIG. 19 (a) shows the intensity obtained when the angle of incidence is 0° and 5°, FIG. 19 (b) shows the intensity obtained when the angle, of incidence is 10° and 15°, FIG. 19 (c) shows the intensity obtained when the angle of incidence is 20° and 25°, and FIG. 19 (d) shows the intensity obtained when the angle of incidence is 30° and 35°.

FIG. 22 is a chart showing 2-dimensional intensity distribution of 90 GHz waves having transmitted the copy paper shown in FIG. 20 and been polarized in Y direction at the angle of incidence of 45°

FIG. 23 is a chart showing 2-dimensional intensity distribution of 90 GHz waves having transmitted the copy paper shown in FIG. 20 and been polarized in X direction at the angle of incidence of 15°.

FIG. 24 is a chart showing 2-dimensional intensity distribution of 90 GHz waves having transmitted the copy paper shown in 20 and been polarized in X direction at the angle of incidence of 45°.

FIG. 25 is a chart showing 2-dimensional intensity distribution of 90 GHz waves having been reflected from the copy paper shown in FIG. 18 and polarized in X direction at the angle of incidence of 45°.

FIG. 26 is a chart showing 2-dimensional intensity distribution of 140 GHz waves having transmitted high-quality paper to which the tape shown in FIG. 18 is attached and been polarized Y direction at the angle of incidence of 15°.

DESCRIPTION OF EMBODIMENTS

Embodiments of the present invention will be described by referring to drawings, but the scope of the present invention is not limited to these embodiments but can be modified as required. In particular, the shape, dimensions, positional relations, etc. of each member listed on the drawings show conceptual matter only, and can be modified depending on applications. The same or corresponding members and units in each drawing are provided with identical symbols.

First Embodiment

Figure 1:
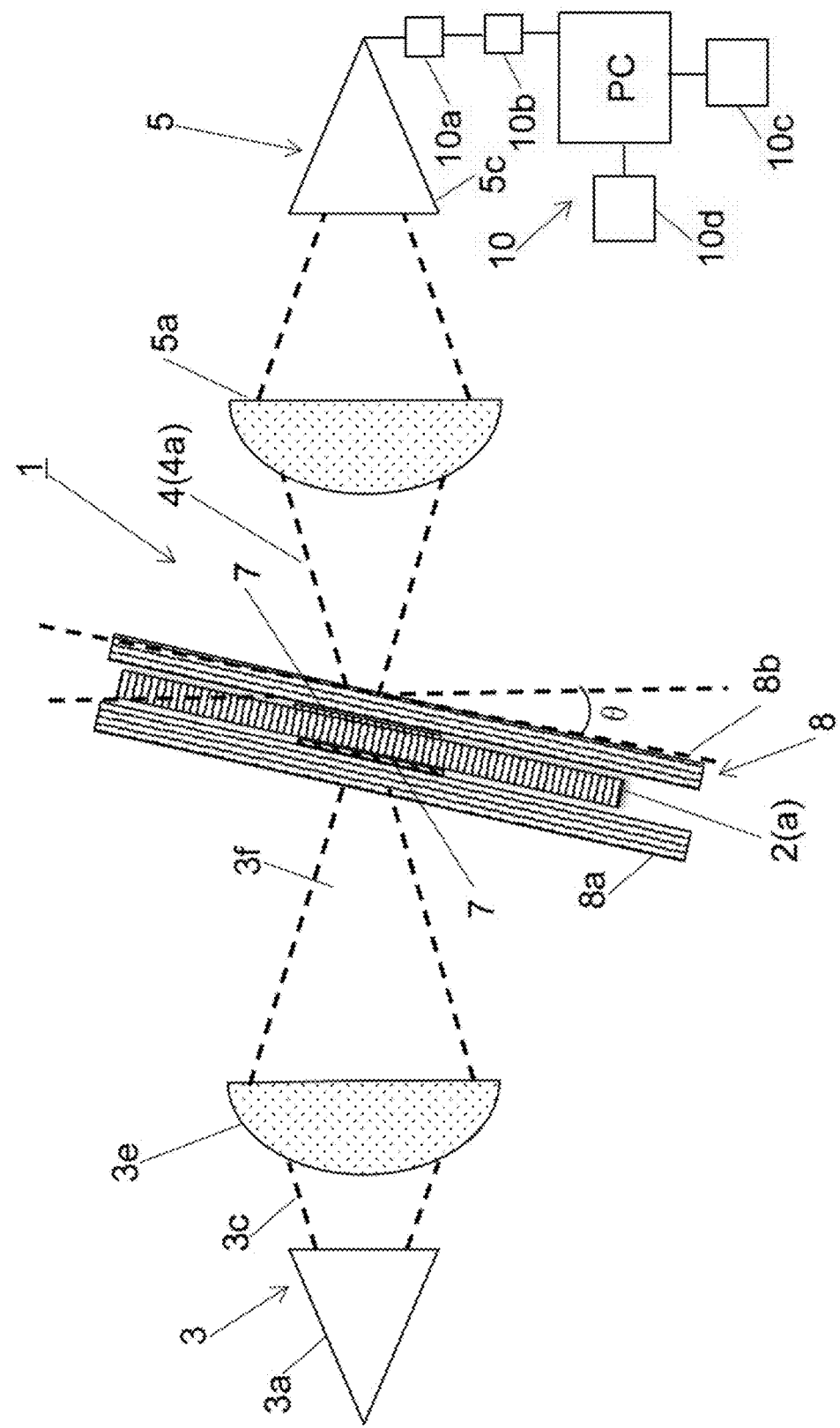
FIG. 1 is a drawing describing an inspection device according to a first embodiment of the present invention.

FIG. 1 is a drawing describing an inspection device 1 according to a first embodiment of the present invention.

As shown in FIG. 1, the inspection device of the present invention 1 includes: a THz wave irradiation unit 3 for irradiating a specimen 2 with THz waves; a THz wave sensing unit 5 for detecting transmitted waves 4 of the THz waves emitted to the specimen 2; and an information processing unit 10 for acquiring intensity distribution of the transmitted waves 4 of the specimen 2 from the intensity data of the transmitted waves 4 of the specimen 2 irradiated with THz waves. The specimen 2 is a sheet of paper, for example. A foreign matter 7 adhering to the specimen is a resin tape for example. This specification assumes that the specimen 2 is a sheet of paper, and the foreign matter 7 is a resin tape.

The THz wave irradiation unit 3 includes: a THz wave oscillator 3a, and a light-collecting optical component 3e for collecting THz waves 3c emitted by the THz wave oscillator 3a to the specimen 2. The present invention assumes the THz waves 3c to have frequency band in a range from 30 GHz (GHz: $10^9$ Hz) to 12 THz.

As an oscillation device used for the THz wave oscillator 3a, various diodes such as Gunn diode, IMPATT diode, and TUNNET diode, and transistors made of Si and compound semiconductors such as GaAs, and InP can be used. As the oscillation device, an integrated circuit made of the above diodes and transistors may also be used. These integrated circuits include the one made of compound semiconductors such as GaAs, and CMOS integrated circuit using Si and SiGe. The CMOS integrated circuit using Si is also called millimeter-wave CMOSIC.

The THz waves 3c are emitted from the THz oscillator 3a to the sheet of paper 2 via a lens as a light-collecting optical component 3e. As the light-collecting optical component 3e, a Fresnel lens, convex lens, concave lens, and a condenser using a mirror can be used. As the mirror, semi-transparent mirror, parabolic mirror, etc. can be used. As the materials of the lens 3e, fluorocarbon resin, glass, etc. can be used. It is preferable that the THz waves 3c be emitted from the THz oscillator 3a at an angle of incidence (θ) with respect to the vertical direction (thickness direction) of the sheet of paper 2. The case where θ is 0° is defined as vertical incidence. When the incidence is vertical or near vertical, a periodic transmission intensity pattern appears due to interference between reflected waves and incident waves into the sheet of paper 2, inhibiting identification of attached objects, which is undesirable. The angle of incidence can be set from several to 50 degrees. The angle of incidence is preferably 10 degrees or more.

Collected THz waves 3f pass through the sheet of paper 2, and fall on a THz wave sensing unit 5 for detecting transmitted waves 4 via a lens 5a, which is light-collecting optical component. As the lens 5a, a Fresnel lens, convex lens, concave lens, and a condenser using a mirror can be used. As the mirror, the semi-transparent mirror, the parabolic mirror, etc. can be used. As materials for the lens and the mirror, fluorocarbon resin, glass, etc. can be used. As the THz wave sensing unit 5, a device that can detect THz waves 4 having passed the sheet of paper and a THz wave receiving circuit can be used. As the THz wave detection device 5c used for the THz wave sensing unit 5, a point-contact diode, a Schottky barrier diode, and a receiving IC can be used. The receiving IC employing heterodyne or homodyne detection system can be used. When the receiving IC employs homodyne detection system, signals branching from the THz wave oscillator 3a of the THz wave irradiation unit 3 may be used as the signals for local oscillators of the receiving IC.

The information processing unit 10 for acquiring intensity distribution of the transmitted waves 4 through the specimen 2 includes: a microcomputer such as microprocessor and microcontroller; or a personal computer. The output from the THz wave sensing unit 5 is input into the microcomputer or the personal computer via an A/D converter 10a and an input/output interface (I/O) 10b. A display 10c and a storage device 10d may be provided as required.

The information processing unit 10 can detect whether the foreign matter 7 is adhering to the specimen 2 at the time of inspection by acquiring 2-dimensional intensity distribution of transmitted waves 4 and comparing the intensity distribution obtained when the sheet of paper without attachment of the foreign matter 7 is detected and the intensity distribution obtained when the sheet of paper 2 is detected at the time of inspection.

The information processing unit 10 may store the data acquired in advance by measuring 2-dimensional intensity distribution when transmitted waves 4 from the sheet of paper 2 without attachment of the foreign matter 7 is detected in the storage device 10d of the information processing unit 10 as reference data. A plurality of reference data may be stored in the storage device 10d of the information processing unit 10 depending on the types of the sheet of paper 2.

Example of Measurement of Transmitted Waves at 90 GHz

An example of measurement by the inspection device 1 shown in FIG. 1 will be described.

As the THz wave oscillator 3a, the Gunn diode oscillator capable of continuously oscillating 90 GHz waves (CW oscillation) (SPACER LABS, model GW-900P) was used. The output of the Gunn diode oscillator is approximately 10 mW. The output of THz waves 3c from the Gunn diode oscillator 3a is collected using a Teflon (registered trademark) lens 3e, and emitted to a Singapore dollar bill 2a. The THz waves 4 having transmitted to the Singapore dollar bill 2a is collected by a Teflon (registered trademark) lens 5a, and the intensity of the transmitted THz waves 4 was detected by the Schottky barrier diode (millitech, model DXP-10-RPFO).

To facilitate maintaining the position, etc. of the Singapore dollar bill 2a, optical resin films 8a, 8b, which allow THz waves to pass through, were attached on both sides of the Singapore dollar bill 2a. As the optical resin films 8a, 8b, cycloolefin polymer (ZEON CORPORATION, ZEONEX (registered trademark)) was used.

Figure 2:
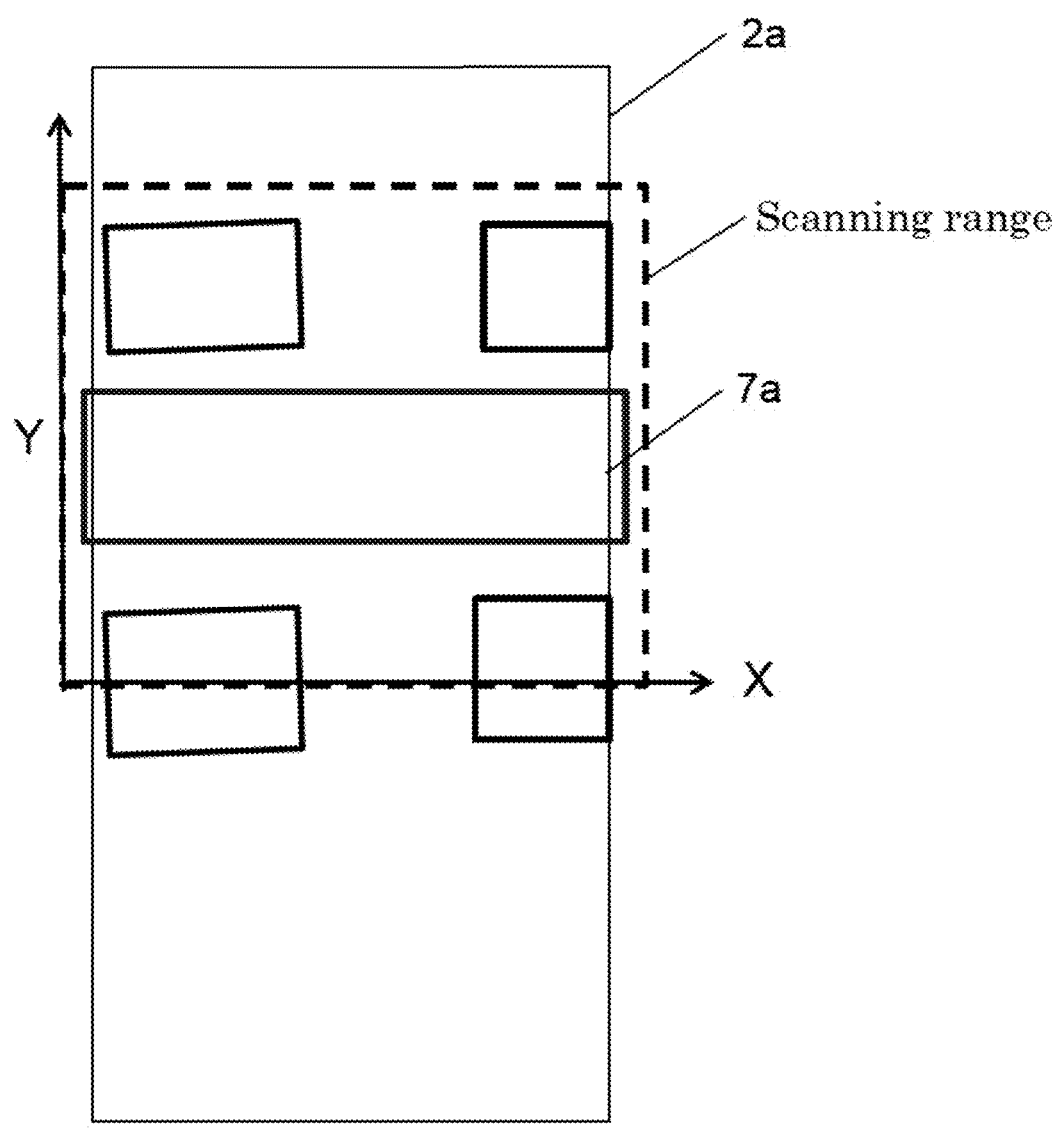
FIG. 2 is a drawing showing the position of attaching a mending tape to a sheet of paper used for measurement.

FIG. 2 is a drawing showing the position of attaching a mending tape 7a to the sheet of paper used for measurement. As shown by this figure, 64 mm×18 mm mending tape 7a was attached to the front and back faces of the Singapore dollar bill 2a. The width of the Singapore dollar bill 2a was 64 mm, and the intensity distribution of the transmitted waves 4 was measured at every 2 mm in a range of approximately 70 mm (X direction)×60 mm (Y direction). The thickness of the Singapore dollar bill 2a was approximately 0.1 mm (100 μm). The sheet of paper 2 was transferred in Y direction, but it may be transferred in X direction.

Figure 3:
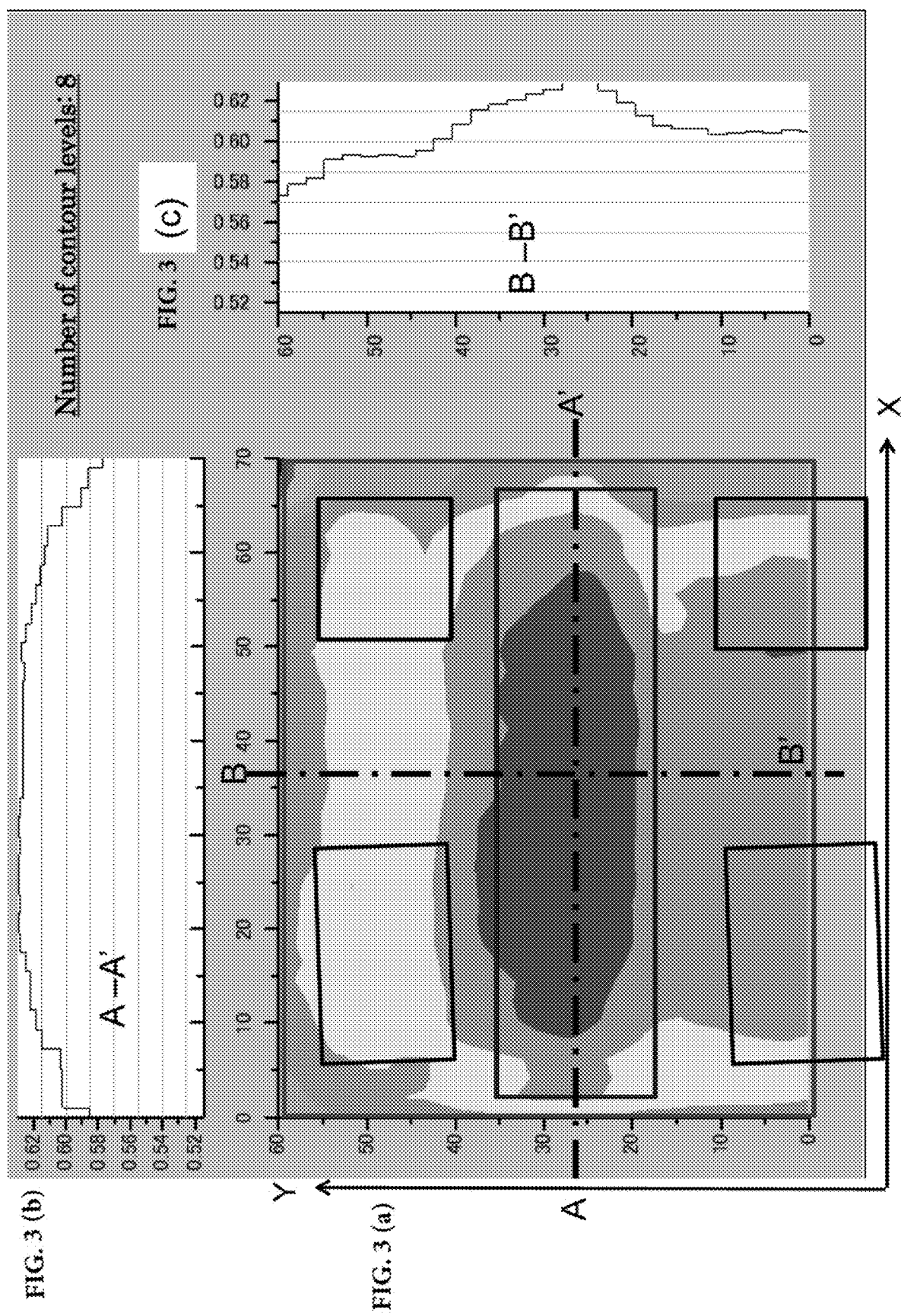
FIG. 3 (a) to FIG. 3 (c) are charts showing typical 2-dimensional intensity distribution of THz waves having transmitted the sheet of paper acquired by using the inspection device of the present invention, where FIG. 3 (a) is the 2-dimensional intensity distribution, FIG. 3 (b) is the intensity distribution in a direction along A-A' in FIG. 3 (a), and FIG. 3 (c) is the intensity distribution in a direction along B-B' in FIG. 3 (a).

FIG. 3 (a) to FIG. 3 (c) show an example of 2-dimensional intensity distribution of THz waves having passed the sheet of paper 2 obtained by the inspection device 1 of the present invention, where FIG. 3 (a) is 2-dimensional intensity distribution, FIG. 3 (b) is the intensity distribution in a direction along A-A' in FIG. 3 (a), and FIG. 3 (c) is the intensity distribution in a direction along B-B' in FIG. 3 (a).

Firstly, the 2-dimensional intensity distribution of the transmitted waves 4 was acquired when the Singapore dollar bill 2a was irradiated with the THz waves.

Next, the mending tape 7a having the width of approximately 64 mm and the length of approximately 18 mm was attached as the foreign matter 7 at the same position on the front and back faces of the Singapore dollar bill 2a. The 2-dimensional intensity distribution of transmitted waves 4a was acquired in a state where the mending tape 7a was attached.

FIG. 3(a) compares, by using 8-level contour lines, the 2-dimensional intensity distribution of transmitted waves 4 through the Singapore dollar bill 2a only with the 2-dimensional intensity distribution of transmitted waves 4a through the Singapore dollar bill 2a to which the mending tape 7a is attached. In this figure, the part with dark gray is where the intensity is higher, which corresponds to the part to which the mending tape 7a is attached. The mending tape 7a is made of an acetate film, etc.

The intensity distribution in the direction along A-A' shown in FIG. 3(b) is the intensity distribution in the width direction (X direction) of the Singapore dollar bill 2a to which the mending tape 7a is attached. It is found that the intensity of the transmitted waves 4a is higher at the position where the mending tape 7a is attached.

The intensity distribution in the direction along B-B' shown in FIG. 3(c) is the intensity distribution in the direction vertical to the width direction (Y direction) of the Singapore dollar bill 2a to which the mending tape 7a is attached. It is found that the intensity of transmitted waves 4a is higher at the position where the mending tape 7a is attached, whereas at the position where the mending tape 7a is not attached, the intensity of the transmitted waves 4a is lower.

The reason why the intensity of transmitted waves 4a increases when the mending tape 7a is attached to the Singapore dollar bill 2a as the foreign matter 7, as shown in FIGS. 2 and 3, will be described.

Figure 4:
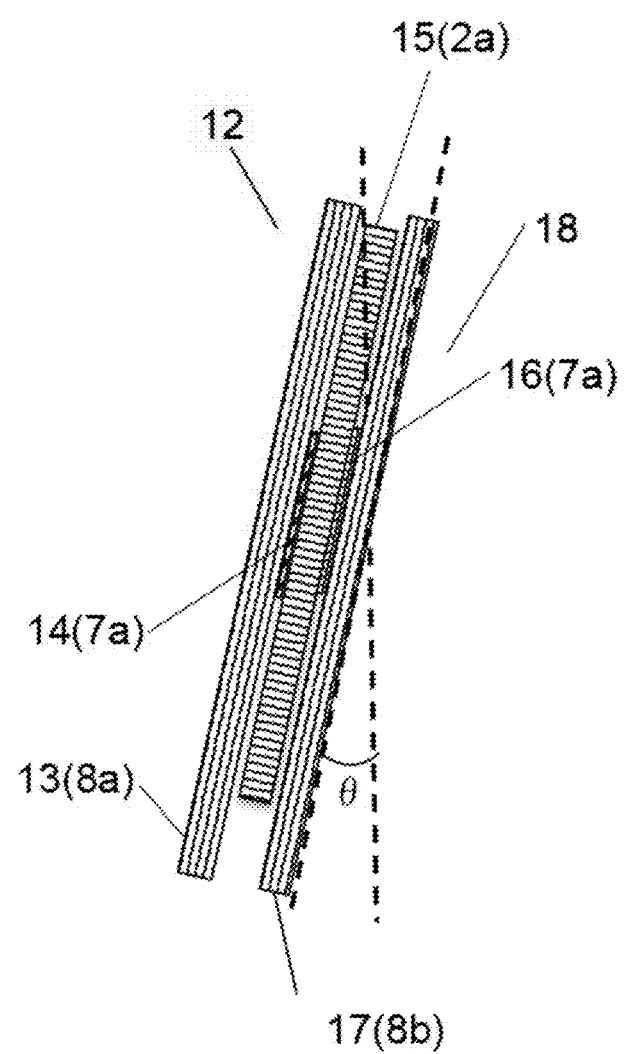
FIG. 4 is a drawing showing a cross section of a medium irradiated with THz waves.

FIG. 4 is a drawing showing the cross section of a medium irradiated with THz waves. The THz waves pass through air (refraction index: $n_0$) as a first medium 12, a first optical resin film 8a (refraction index $n_1$) disposed on the front face of the Singapore dollar bill 2a as a second medium 13, the mending tape 7a (refraction index $n_2$) adhering to the front face of the Singapore dollar bill 2a as a third medium 14, the Singapore dollar bill 2a (refraction index: $n_3$) as a fourth medium 15, the mending tape 7a (refraction index: $n_2$) adhering to the back face of the Singapore dollar bill 2a as a fifth medium 16, a second optical resin film 8b (refraction index: $n_1$) disposed on the back face of the Singapore dollar bill 2a as a sixth medium 17, and air (refraction index: $n_0$) as a seventh medium 18 in that order.

The refraction indices of the above media are:

Refraction index of air, which is the first and the seventh media 12, 18, $(n_0)=1$;

Refraction index of optical resin film 8, which is the second and the sixth media 13, 17, $(n_1)=1.53$;

Refraction index of mending tape 7a, which is the third and the fifth media 14, 16, $(n_2)=1.57$;

Refraction index of Singapore dollar bill 2a, which is the fourth medium 15, $(n_3)=1.45$ to 1.5.

The refraction index of the mending tape 7a ($n_2=1.57$), which adheres to both faces of the Singapore dollar bill 2a and works as the third and the fifth media 14, 16, and the refraction index of the first and the second optical resin films 8a, 8b ($n_1=1.53$), which work as the second and the sixth media 13, 17, are both larger than the refraction index of the Singapore dollar bill 2a ($n_3=1.45$ to 1.5). Consequently, the mending tape 7a (refraction index $n_2=1.57$), which is attached to both faces of the Singapore dollar bill 2a and works as the third and the fifth media 14, 16 is assumed to work as a lens, increasing the intensity of transmitted waves 4a. In other words, foreign matter 7 such as the mending tap 7a adhering to the sheet of paper 2 can be detected from the change in the intensity due to lens effect based on the difference between the refraction index of the foreign matter 7 and the refraction index of the specimen 2 without attachment of foreign matter 7.

The optical resin films 8a, 8b, which work as the second and the sixth media 13, 17, are used to support the Singapore dollar bill 2a. The lens effect described above can be achieved without the first and the second optical resin films 8a, 8b.

Figure 5:
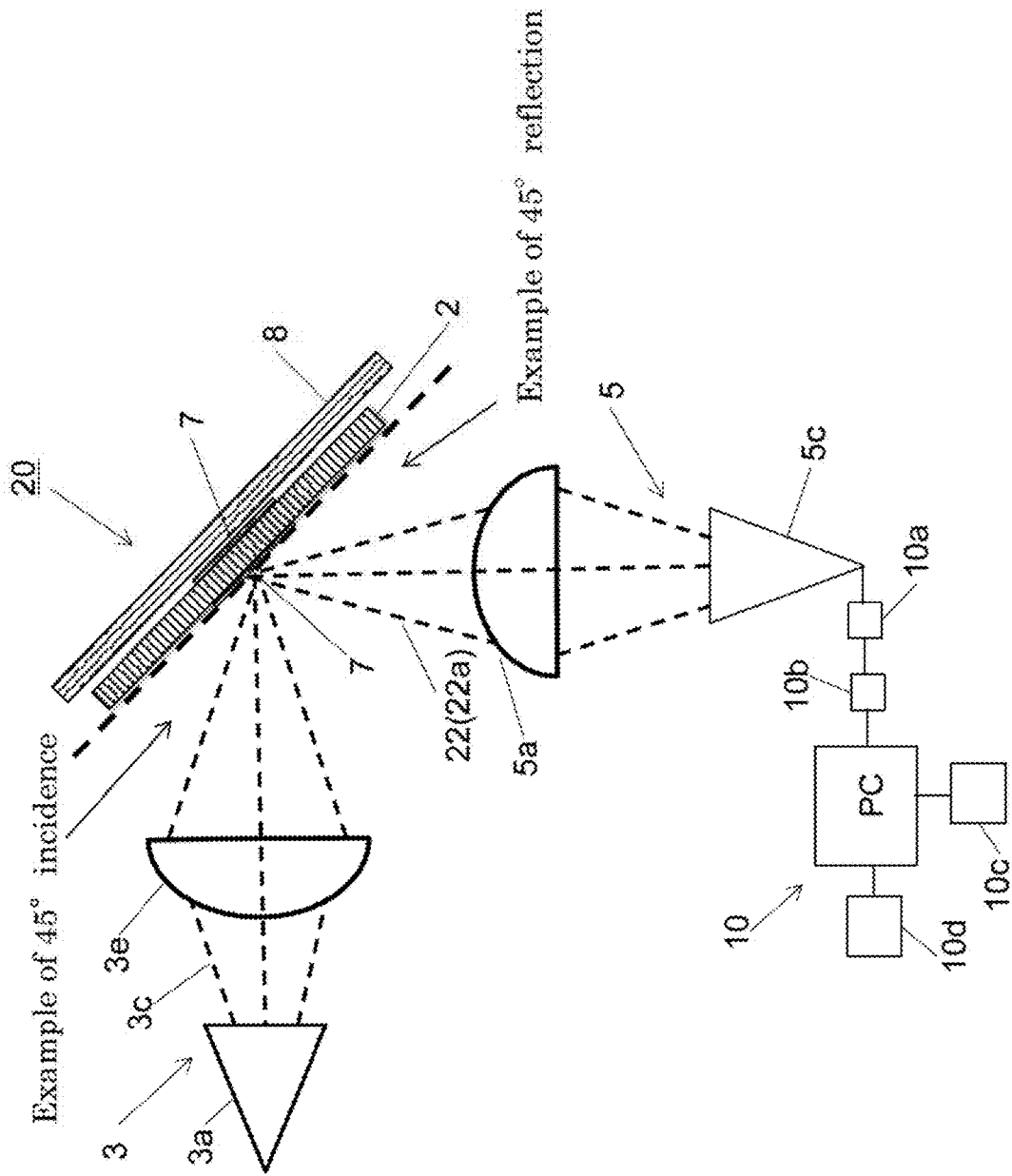
FIG. 5 is a drawing describing another inspection device different from the first embodiment of the present invention.

FIG. 5 is a drawing describing another inspection device 20 according to the first embodiment of the present invention.

This inspection device 20 differs from the inspection device 1 in FIG. 1 in that the THz wave sensing unit 5 detects the reflected waves 22 instead of the transmitted waves 4, 4a of the THz waves through the sheet of paper 2. Since other points are the same as those of the inspection device 1 in FIG. 1, the description will be omitted.

The above inspection device 20 measures the reflected waves 22 of the THz waves emitted to the sheet of paper 2. As in the case of the measurement of transmitted waves 4 described above, the foreign matter 7 such as the mending tape 7a adhering to the sheet of paper 2 can be detected from the change in the intensity due to lens effect based on the difference between the refraction index of the foreign matter 7 and the refraction index of the specimen 2 without attachment of the foreign matter 7.

Example of Measurement of Reflected Waves at 60 GHz

An example of measurement using the above inspection device 20 will be described.

Figure 6:
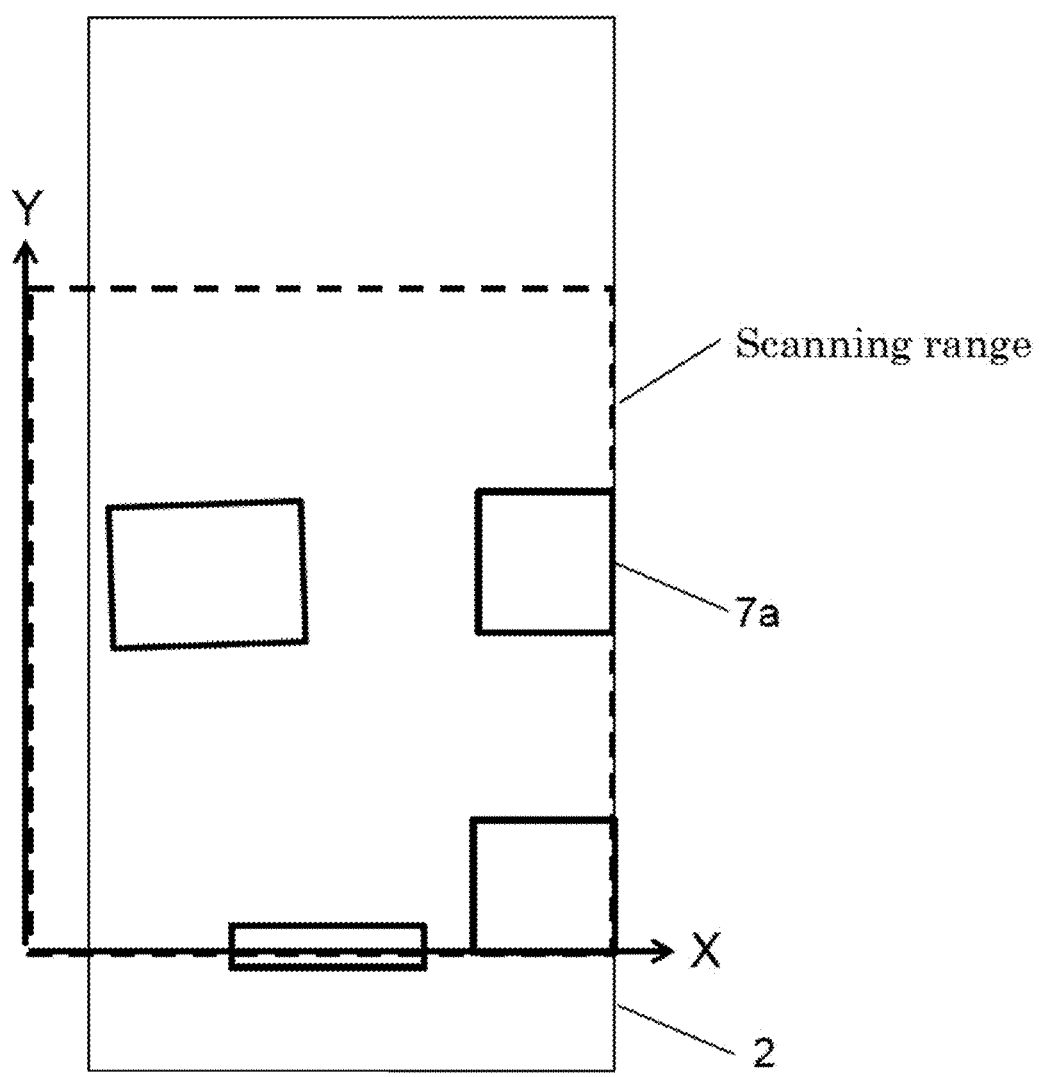
FIG. 6 is a drawing showing the position of attaching the mending tape to a sheet of paper used for 60 GHz reflection measurement.

FIG. 6 is a drawing describing the position of attaching the mending tape 7a to the sheet of paper used for reflected wave measurement at 60 GHz. To the front and the back faces of the Singapore dollar bill 2a, the mending tapes 7a were attached at the following positions: left and right sides of the approximate center of the scanning range, bottom-right corner, and a part of the bottom center area of the scanning range. The mending tape 7a measures 18 mm×20 mm. The intensity distribution of the reflected waves 22 was measured at every 2 mm within the range of 70 mm×80 mm shown in FIG. 6.

As the THz wave oscillator 3a, a continuous-oscillation (CW oscillation) Gunn diode oscillator (model GDO-15-6013R) was used. The output of the Gunn diode oscillator 3a is approximately 10 mW. Measurement was taken in the same manner as the measurement of transmitted waves 4 shown in FIG. 2 except that waves reflected at the angle of 45° with respect to the angle of incidence of 45° were measured. The Schottky barrier diode for 60 GHz (SPACER LABS, model DV-2N) was used for the measurement of the reflected waves.

To facilitate retaining the position, etc. of the Singapore dollar bill 2a, the optical resin film 8 made of cycloolefin polymer (ZEON CORPORATION, ZEONEX [registered trademark]), which allows THz waves to pass through, was disposed on the back face of the Singapore dollar bill 2a.

Figures 7A, 7B, 7C:
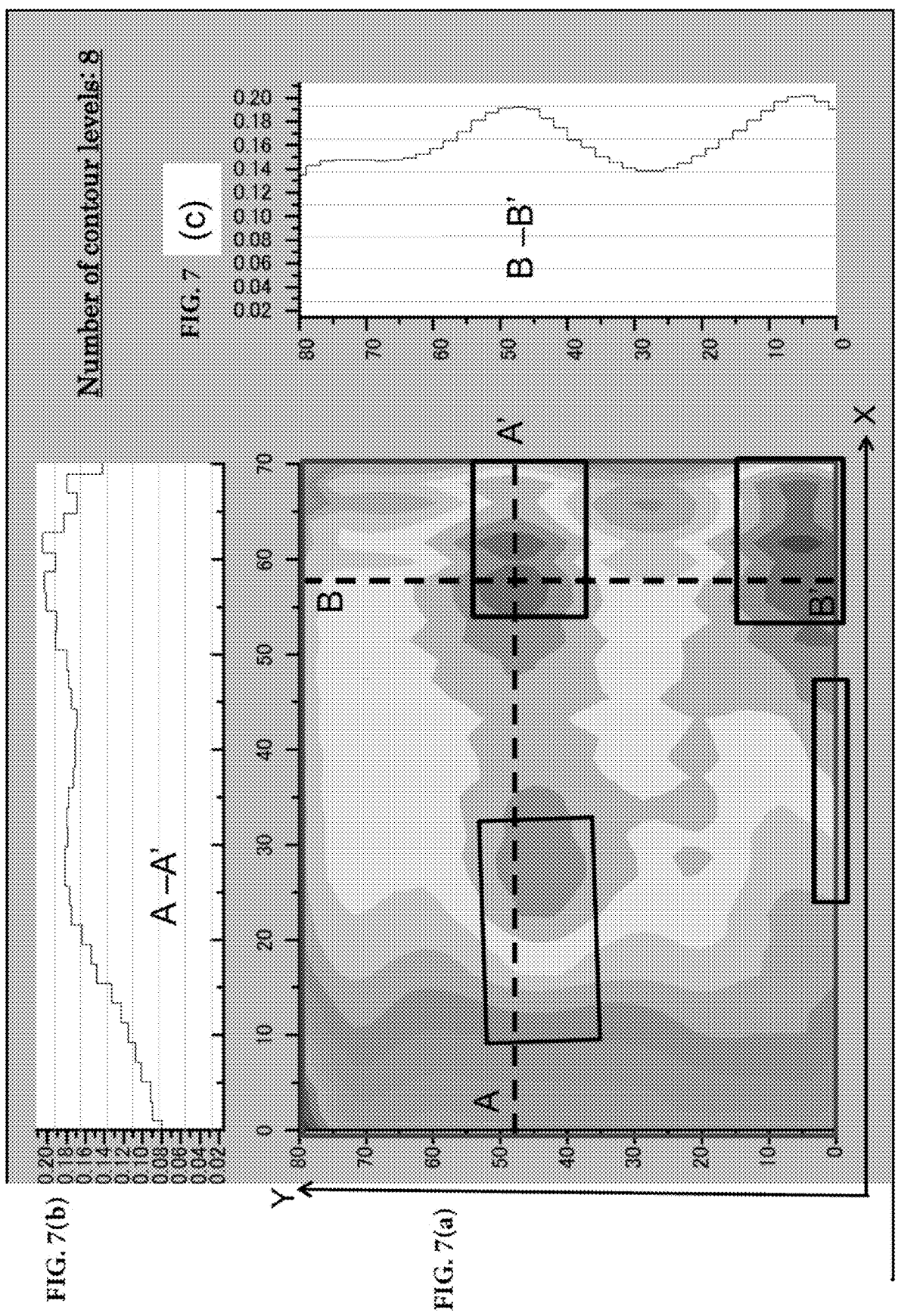
FIG. 7 (a) to FIG. 7 (c) are charts showing typical 2-dimensional intensity distribution of reflected waves from a Singapore dollar bill obtained at 60 GHz, where FIG. 7 (a) is 2-dimensional intensity distribution, FIG. 7 (b) is the intensity distribution in a direction along A-A' in FIG. 7 (a)_ and FIG. 7 (c) is the intensity distribution in a direction along B-B' in FIG. 7 (a).

FIG. 7 (*a*) to FIG. 7 (*c*) are charts showing the 2-dimensional intensity distribution of reflected waves 22 from the Singapore dollar bill 2a obtained at 60 GHz, where FIG. 7 (*a*) is 2-dimensional intensity distribution. FIG. 7 (*b*) is the intensity distribution in a direction along A-A' in FIG. 7 (*a*), and FIG. 7 (*c*) is the intensity distribution in a direction along B-B' FIG. 7 (*a*).

Firstly, the 2-dimensional intensity distribution of the reflected waves 22 was acquired by irradiating the Singapore dollar bill 2a with THz waves.

Then by attaching the mending tapes 7a to the Singapore dollar bill 2a, the 2-dimensional intensity distribution of the reflected waves 22 was obtained.

FIG. 7(*a*) compares, by using 8-level contour lines, the 2-dimensional intensity distribution of the reflected waves 22 from the Singapore dollar bill 2a only and the 2-dimensional intensity distribution of the reflected waves 22a from the Singapore dollar bill to which the mending tapes 7a were attached. In this figure, the part shown as dark gray is where the intensity of the transmitted waves 4 is higher, which corresponds to four positions of the Singapore dollar bill 2a where the mending tapes 7a were attached.

The 1-dimensional intensity distribution in the direction along A-A' (X direction) shown in FIG. 7(*b*) is the intensity distribution on the mending tape 7a in the width direction of the Singapore dollar bill 2a, which shows that the intensity of the reflected waves 22a is high at the part of the Singapore dollar bill 2a where the mending tape 7a is attached.

The intensity distribution in the direction along B-B' shown FIG. 7 (*c*) is the intensity distribution on the mending tape 7a in the direction vertical to the width direction of the Singapore dollar bill 2a (direction), which shows that the intensity of reflected waves 22a is higher in the part where the mending tape 7a is attached and that the intensity of the reflected waves 22a is lower at the part of the Singapore dollar bill 2a where the mending tape 7a is not attached.

The intensity of transmitted waves 4 and reflected waves 22 changes depending on the thickness and material of the sheet of paper 2, the thickness and the material of the foreign matter 7, etc. The intensity of transmitted waves 4 and reflected waves 22 also changes depending on the frequency and the direction of polarization of the THz waves used and the angle of incidence of the THz waves into the sheet of paper 2. Consequently, it is desirable that adjustment be made by any one of the frequency, the polarization, and the angle of incidence to the sheet of paper 2, or by combination of those, depending on the sheet of paper 2 to be inspected and the foreign matter 7 to be detected. The THz wave oscillator 3a may be equipped with a THz oscillator capable of generating two or more frequencies so that the optimum THs waves can be generated to each sheet of paper 2 even when the sheet of paper 2 is changed. It is only necessary to make an adjustment in accordance with the polarization of the THz waves fallen on the sheet of paper 2 so that the state of polarization can be detected sensitively by the THz wave sensing unit 5.

Second Embodiment

As a second embodiment of the present Invention, an inspection device 30 that can detect the foreign matter 7 adhering to the sheet of paper 2 by transferring and scanning the sheet of paper 2 in the direction vertical to the width direction (Y direction) will hereafter be described.

Figure 8:
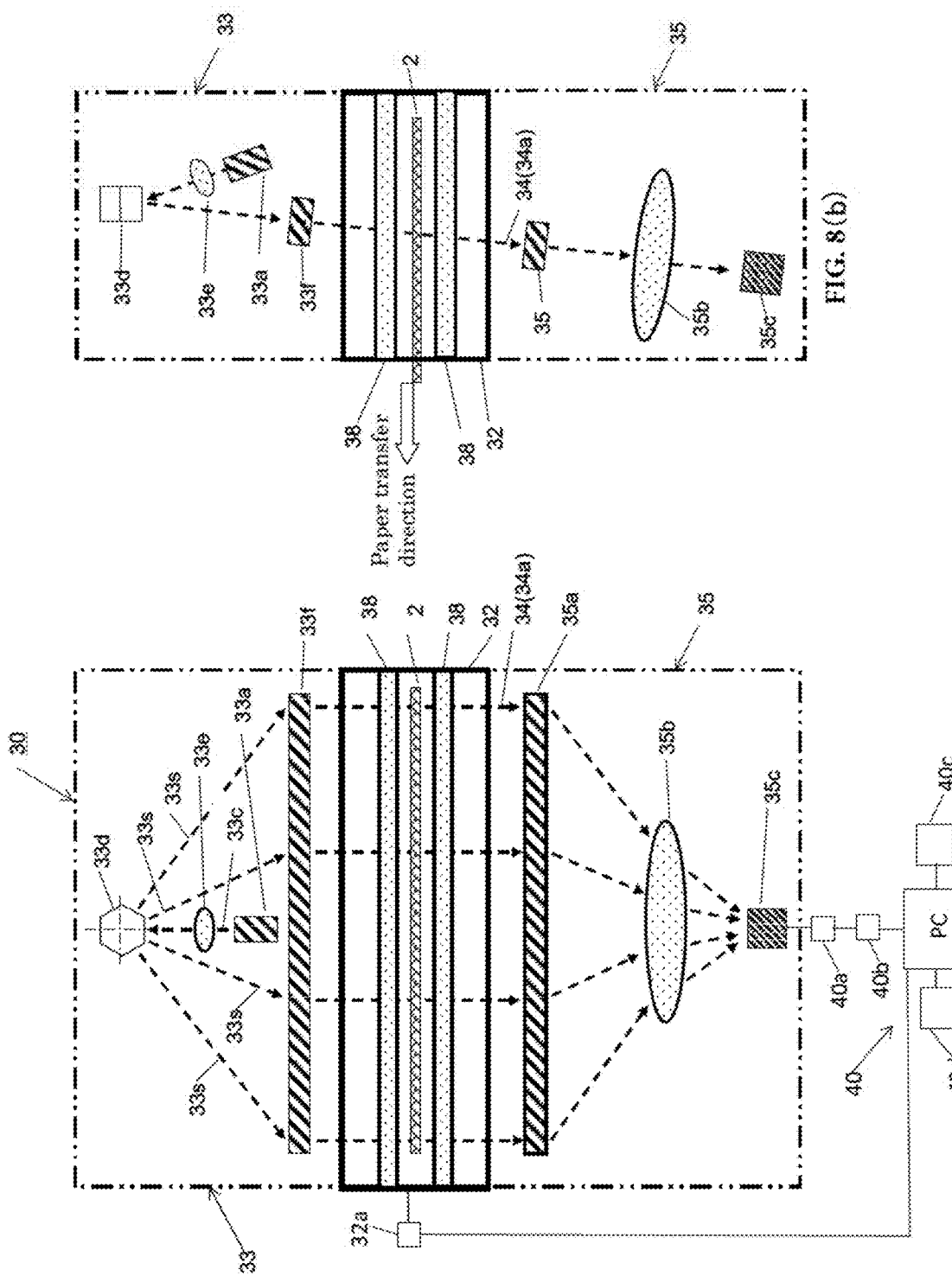
FIG. 8 (a) and FIG. 8 (b) are drawings describing an inspection device according to a second embodiment of the present invention, where FIG. 8 (a) is a front view, and FIG. 8 (b) is a right-side view.

FIG. 8 (*a*) and FIG. 8 (*b*) are drawings describing the inspection device 30 according to the second embodiment of the present invention, where FIG. 8 (*a*) is a front view, and FIG. 8 (*b*) is a right-side view. This inspection device 30 includes: a paper transfer unit 32 for transferring the sheet of paper 2; a THz wave irradiation unit 33 for emitting THz waves in a direction orthogonal to the transfer direction of the paper transfer unit 32; a THz wave sensing unit 35 for detecting transmitted waves 34 of the THz waves falling onto the sheet of paper 2; and an information processing unit 40 for acquiring intensity distribution of the transmitted waves 34 through the sheet of paper 2 from the it data of the transmitted waves 34 through the sheet of paper 2 irradiated with the THz waves in a direction orthogonal to the transfer direction of the paper transfer unit 32.

As shown in FIG. 8 (a) and FIG. 8 (b), the THz wave irradiation unit 33 includes: a THz wave oscillator 33a; and a scanning device 33d for scanning the THZ waves 33c emitted from the THz wave oscillator 33a. THz, waves from the oscillation device using a Gunn diode of the THz wave oscillator 33a are collected by a lens 33e, etc., scanned by the scanning device 33d from the left end to the right end in the width direction (X direction in FIG. 2) of the sheet of paper 2, and furthermore emitted to the sheet of paper 2 transferred by the paper transfer unit 32 via a Fresnel lens 33f, etc.

As the scanning device 33d, any one of galvanometer mirror, polygon mirror, and digital mirror devices can be used.

The Fresnel lens 33f has the function of emitting THz waves 33s scanned by the scanning device 33d to the sheet of paper 2 as parallel transmitted waves 34 at an angle of incidence (θ) slightly angled with respect to the vertical direction, which is preferably several to 50°, and more desirably approximately from 10° to 50°, as described previously.

The THz waves 34 having passed the sheet of paper 2 are detected by the THz wave detection device 35c, which includes the Schottky barrier diode, etc., via a light-collecting optical component 35a and a lens 35b. As the lens, Fresnel lens, convex lens, concave lens, etc., and a condenser using a mirror can be used. As the mirror, a semitransparent mirror, parabolic mirror, etc. can be used.

As the light-collecting optical component 35a, Fresnel lens, etc. can be used. The Fresnel lens has a function of collecting THz waves 34 that have passed the sheet of paper 2 at a predetermined angle and have become transmitted waves into the lens 35b.

The paper transfer unit 32 includes a transfer mechanism (not shown) for transferring the sheet of paper 2. The paper transfer unit 32 transfers the sheet of paper 2 in a direction orthogonal to the direction of scanning of the sheet of paper 2 by the THz waves (X direction), namely Y direction, of the sheet of paper 2 (see FIG. 2). As the paper transfer unit 32, a member material for transferring the sheet of paper 2, resin, and glass 38 can be used. In other words, to transfer the sheet of paper, a member made of a material that allows the THz waves to pass through is disposed on the top or the bottom face, or on both faces, of the sheet of paper 2. As the glass 38, the inorganic glass or the organic glass that transmits THz waves can be used. In order to increase the intensity of transmitted waves 34 or reflected waves 52, which will be described later, by the lens effect due to the difference in refraction indices described previously, it is desirable that the refraction index of the resin or glass 38 be larger than that of the sheet of paper 2. The scanning direction was Y direction of the sheet of paper 2, but X direction is also allowed.

The information processing unit 40 can detect whether the foreign matter 7 is adhering to the sheet of paper 2 by comparing the 2-dimensional intensity distribution of the transmitted waves 34 acquired when the sheet of paper 2 without attachment of the foreign matter 7 is detected and the 2-dimensional intensity distribution of the transmitted waves 34a acquired when the sheet of paper 2 to which foreign matter 7 is attached is detected at the time of inspection.

Figure 9:
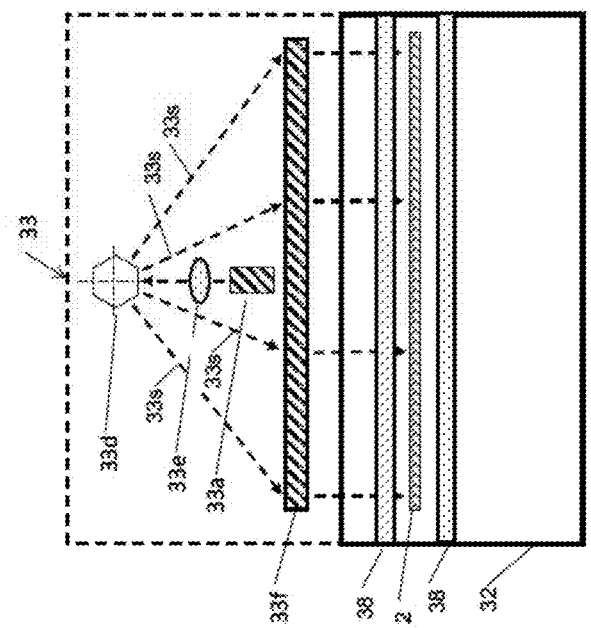
FIG. 9 (a) to FIG. 9 (c) are drawings describing another inspection device according to the second embodiment of the present invention, where FIG. 9 (a) is a front view, FIG. 9 (b) is a right-side view, and FIG. 9 (c) is a rear view.
Figure 9:
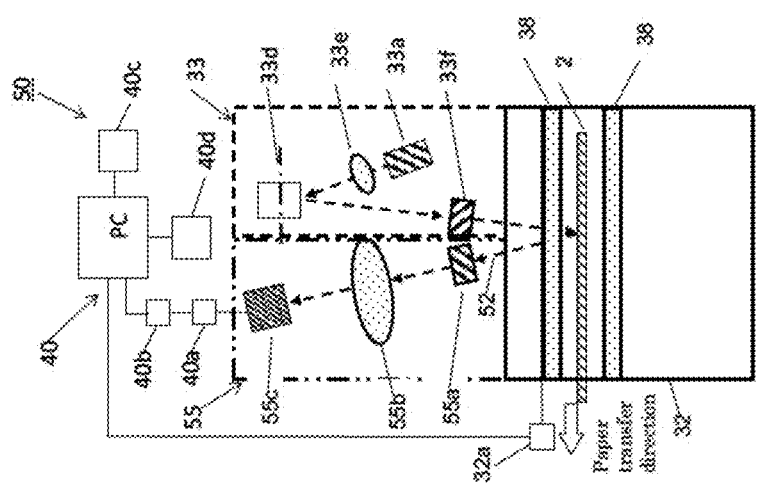
Figure 9:
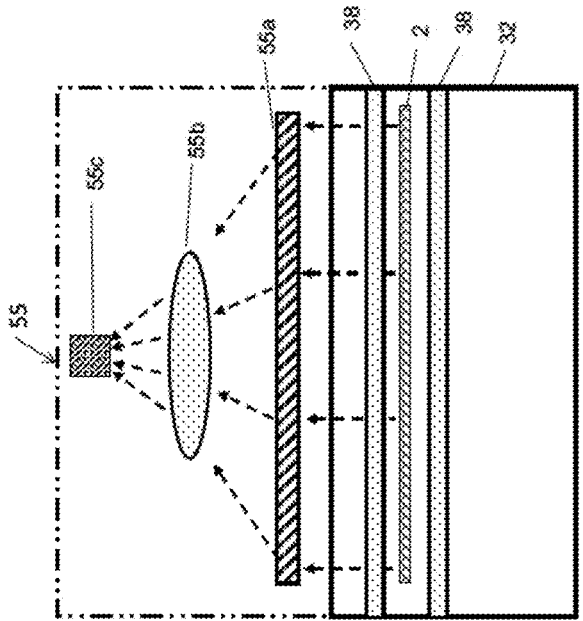

FIG. 9 (a) to FIG. 9 (c) arm drawings describing another inspection device 50 according to the second embodiment of the present invention, where FIG. 9 (a) is a front View. FIG. 9 (b) is a right-side view, and FIG. 9(c) is a rear view.

This inspection device 50 differs from the inspection device 30 shown in FIG. 8(a), and FIG. 8 (b) in that reflected waves 52 of the THz waves are detected. The THz wave sensing unit 55 for detecting reflected waves 52 of the THz waves includes: a light-collecting optical component 55a for collecting transmitted THz waves 52 reflected from the sheet of paper 2; and a THz wave detection device 55c made of a Schottky barrier diode etc. for detecting reflected waves 52 of the THz waves via a lens 55b. The structure of the THz wave sensing unit 55 is the same as the THz wave sensing unit 35 shown in FIG. 8 (a) and FIG. 8 (b), but disposed on the upper side of the paper transfer unit 32. Since other structures are the same as those of the inspection device 30 shown in FIG. 8 (a) and FIG. 8 (b), the description will be omitted.

In the inspection devices 30, 50 according to the second embodiment shown in FIGS. 8 and 9, the information processing unit 40 includes a microprocessor, microcontroller, and personal computer, as in the case of the inspection devices 1, 20. The output from the THz wave sensing unit 55 is input into the microprocessor or personal computer via an A/D converter 40a and an input/output interface (I/O) 40b. The information processing unit 40 may further include a display 40c and a storage device 40d.

The output from the THz wave sensing unit 55 and the information on the transfer position of the sheet of paper 2 from the sheet transfer unit 32, etc. are input to the information processing unit 40.

When the scanning is performed by the THz waves emitted from the THz wave irradiation unit 33 from the left end to the right end in the width direction of the sheet of paper 2 (X direction), the paper transfer unit 32 transfers the sheet of paper 2 to a next scanning position. In other words, the sheet of paper 2 is transferred to the next scanning position, Y direction. This transfer of the sheet of paper 2 can be achieved by a transfer mechanism using a belt and motor and the transfer mechanism using a step motor (not shown).

The transfer of each sheet of paper 2 in Y direction may be judged whether the sheet of paper 2 passes the scanning position or not. Passing of the sheet of paper 2 in Y direction can be detected using a photo coupler or a photo interrupter provided to the paper transfer unit 32.

While the sheet of paper 2 passes in Y direction from one end to the other end of the sheet of paper, the 2-dimensional intensity distribution of the THz waves transmitted or reflected from the sheet of paper 2 is calculated from the output intensity signal of transmitted THz waves 34 or reflected THz waves 52.

As described above, the output from the THz wave sensing unit 35, 55 and the information on the transfer position of the sheet of paper 2 from the paper transfer unit 32, etc. are input from a control circuit 32a of the paper transfer unit 32 to the information processing unit 40, which then outputs the 2-dimensional intensity distribution by the transmitted waves 34 or reflected waves 52 of the THz waves from the sheet of paper 2 passing the paper transfer unit 32.

When the sheet of paper 2 is judged not to be normal based on the 2-dimensional intensity distribution of the transmitted waves 34 and reflected waves 52 of the THz waves from the sheet of paper 2 passing the paper transfer unit 32, the sheet of paper may be withdrawn by a recovery unit as the paper has been judged to be abnormal.

According to this inspection device 30, 50, since one side of the sheet of paper 2 (X direction) can be scanned by one THz wave oscillator 33a and the sheet of paper is transferred sequentially to the other side (Y direction), the foreign matter 7 adhering to the sheet of paper 2 can be detected without contact, at high speed, highly efficiently, and at low cost based on the 2-dimensional intensity distribution of the 2-dimensional transmitted waves 34 and reflected waves 52 of the THz waves falling on the sheet of paper 2. In other words, since one side of the sheet of paper 2 can be scanned by one THz wave oscillator 33a, a plurality of THz wave oscillators or THz wave detectors for scanning are unnecessary.

Third Embodiment

A detection device using a plurality of THz wave oscillators or a plurality of THz wave detectors will then be described.

Figure 10B:
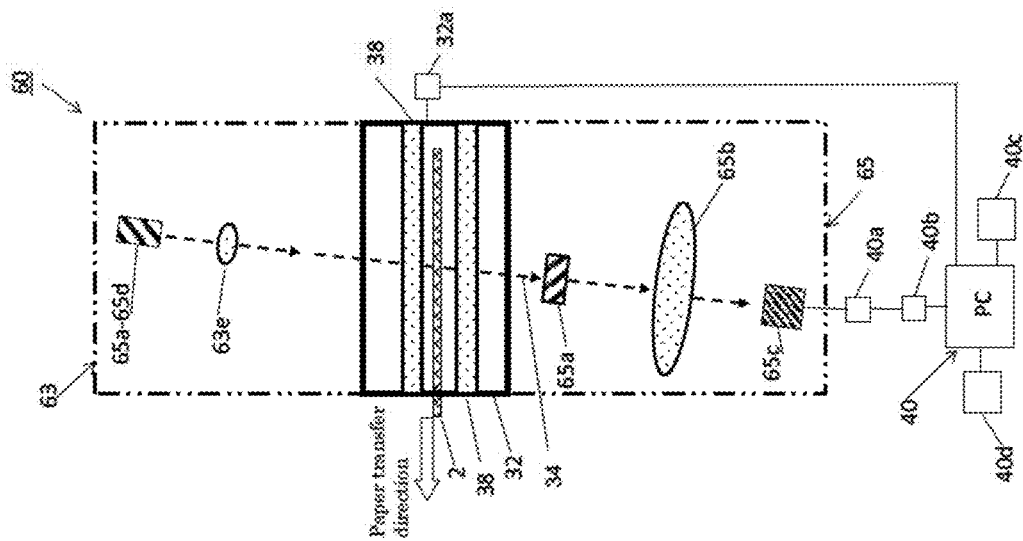
FIG. 10 (a) and FIG. 10 (b) are drawings describing an inspection device according to a third embodiment of the present invention, where FIG. 10 (a) is a front view, and FIG. 10 (b) is a right-side view.
Figure 10A:
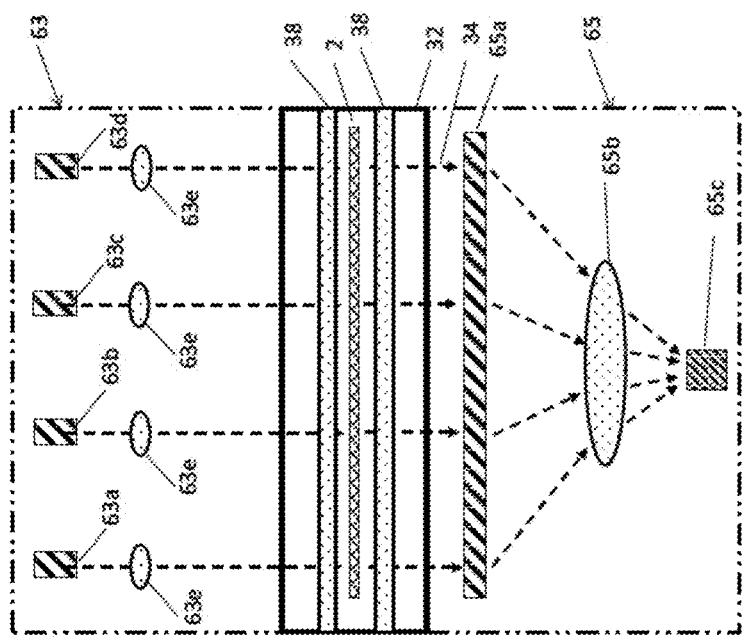

FIG. 10 (a) and FIG. 10 (b) are drawings describing an inspection device 60 according to a third embodiment of the present invention, where FIG. 10 (a) is a front view, and FIG. 10 (b) is a right-side view. This inspection device 60 is structured to detect transmitted waves 34 as in the case of the inspection device 30 shown in FIG. 8 (a) and FIG. 8 (b), but differs from the inspection device 30 in that a THz wave irradiation unit 63 made of a plurality of THz wave oscillators 63a-63d is provided. Since other structures are the same as those of the inspection device 30 shown in FIG. 8 (a) and FIG. 8 (b), the description will be omitted.

Specifically, the THz wave irradiation unit 63 includes: a plurality of THz wave oscillators 63a, 63b, 63c, 63d, and lenses 63e inserted between the plurality of THz wave oscillators 63 and the paper transfer unit 32. The THz waves from each THz wave oscillator 63a, 63b, 63c 63d are collected by each corresponding lens 63e, and emitted to the sheet of paper 2 transferred in the width direction (X direction in FIG. 2) by the paper transfer unit 32.

The plurality of THz wave oscillators 63a, 63b, 63c, 63d may be controlled by the information processing unit 40 so as to generate pulses in the width direction of the sheet of paper 2 (X direction in FIG. 2) in predetermined order. For example, the THz wave oscillators 63a, 63b, 63c, 63d are made to generate pulses in that order, the sheet of paper 2 is then transferred in the transfer direction (Y direction in FIG. 2) for a specified distance, and then the THz wave oscillators 63a, 63b, 63c, 63d are made to generate pulses sequentially again. By repeating this operation, the sheet of paper 2 can be 2-dimensionally scanned.

The THz wave sensing unit 65 is structured similarly as the THz wave sensing unit 35 shown in FIG. 8 (a) and FIG. 8 (b), and the detection is performed by the THz wave sensing unit 65 made of Schottky barrier diode, etc., which is a THz wave detection device 65c, via a light-collecting optical component 65a made of a Fresnel lens etc. and a lens 65b. Since other structures are the same as those of the inspection device 30 shown in FIG. 8 (a) and FIG. 8 (b), the description will be omitted.

Transmitted waves 34 of the THz waves from each THz wave oscillator 63a, 63b, 63c, 63d disposed in the width direction of the sheet of paper 2 (X direction in FIG. 2) are made to fall on the THz wave sensing unit 65 sequentially, and by 2-dimensionally scanning the sheet of paper 2, the 2-dimensional signal distribution of the transmitted waves 34 of the THz waves can be acquired.

According to the inspection device 60 in the third embodiment, since the THz wave irradiation unit 63 includes a plurality of THz wave oscillators 63a, 63b, 63c, 63d and a plurality of lenses 63e, and does not include a scanning device, downsizing is achieved. Furthermore, since the scanning device having the driving part is not used, the reliability increases.

(Modification 1 of the Third Embodiment)

FIG. 11 (al) to FIG. 11 (c) are drawings describing an inspection device 70 according to modification 1 of the third embodiment of the present invention, where FIG. 11 (a) is a front view, FIG. 11(b) is a right-side view, and FIG. 11(c) is a rear view. This inspection device 70 is structured to detect reflected waves 52 as in the case of the inspection device 50 shown in FIG. 9 (a) to FIG. 9 (c), but is different from the inspection device 50 in that a THz wave irradiation unit 73 made of a plurality of THz wave oscillators is provided. Since other structures are the same as those of the inspection device 50 shown in FIG. 9 (a) to FIG. 9 (c), the description will be omitted.

Specifically, the THz wave irradiation unit 73 includes: a plurality of THz wave oscillators 73a, 73b, 73c, 73d; and lenses 73e inserted between the plurality of THz wave oscillators 73 and a paper transfer unit 32. The THz waves from each THz wave oscillator 73a, 73b, 73c, 73d are collected by the lenses 73e, and emitted in the width direction of the sheet of paper 2 (X direction in FIG. 2) transferred by the paper transfer unit 32.

The plurality of THz wave oscillators 73a, 73b, 73c, 73d may be controlled by the information processing unit 40 so as to generate pulses sequentially in the width direction of the sheet of paper 2 (X direction in FIG. 2). For example, the THz wave generators 73a, 73b, 73c, 73d are made to generate pulses in that order, the sheet of paper 2 is transferred in the transfer direction (Y direction in FIG. 2) for a specified distance, and then the THz wave oscillators 73a, 73b, 73c, 73d are made to generate pulses sequentially again. By repeating this operation, the sheet of paper 2 can be 2-dimensionally scanned.

As the case of the THz wave sensing unit 35 shown in FIG. 8 (a) and FIG. 8 (b), the THz wave sensing unit 75 includes: a light-collecting optical component 75a made of a Fresnel lens, etc.; a lens 75b; and a Schottky barrier diode as a THz wave detection device 75c, and the THz wave sensing unit 75 is disposed above the paper transfer unit 32 so as to detect reflected waves 52 of the THz waves.

The reflected waves 52 of the THz waves from each THz wave oscillator 73a, 73b, 73c, 73d disposed in the width direction of the sheet of paper 2 (X direction in FIG. 2) are made to fall sequentially on the THz wave sensing unit 75, and the 2-dimensional signal distribution of the reflected waves 52 of the THz waves can be acquired by 2-dimensionally scanning the sheet of paper 2.

According to this inspection device 70, since the THz wave irradiation unit 73 includes a plurality of THz wave oscillators 73a, 73b, 73c, 73d and a plurality of lenses 73e, and does not include a scanning device, downsizing is achieved. In addition, since the scanning device having the driving part is not included, the reliability increases.

In the above inspection device 70, the reflected waves 52 of the THz waves from the surface of the sheet of paper 2 are detected, but to detect the reflected waves of the THz waves from the rear face of the sheet of paper 2, another THz irradiation unit 73 and another THz wave sensing unit 75 may be further provided on the bottom side of the paper transfer unit 72.

(Modification 2 of the Third Embodiment)

FIG. 12 (a) and FIG. 12 (b) are drawings describing an inspection device 80 according to modification 2 of the third embodiment of the present invention, where FIG. 12 (a) is a front view, and FIG. 12 (b) is a right-side view. This inspection device 80 is structured to detect the transmitted waves 34 as in the case of the inspection device 30 shown in FIG. 8 (*a*) and FIG. 8 (*b*). The THz wave irradiation unit 83 has the same structure as that of the inspection device 30 using THz band shown in FIG. 8 (*a*) and FIG. 8 (*b*), but is different from the inspection device 30 in that the THz wave sensing unit 85 has a plurality of THz wave detection devices 85*a*, 85*b*, 85*c*, 85*d*.

The THz wave sensing unit 85 is disposed on lower side of the paper transfer unit 32, and a plurality of lenses 85*e* and Schottky barrier diodes, namely a plurality of THz wave detection devices 85*a*, 85*b*, 85*c*, 85*d*, are disposed at positions corresponding to where the THz waves are scanned and transmit the sheet of paper 2.

According to the above inspection device 80, the side of the sheet of paper 2 (X direction) is scanned by one THz wave oscillator 83*a*, and the THz waves having transmitted the sheet of paper are detected by each Schottky barrier diode, namely THz wave detection devices 85*a*, 85*b*, 85*c*, 85*d*. By transferring the sheet of paper 2 sequentially in the direction of the other side (Y), the non-contact detection of foreign matter 7 adhering to the sheet of paper 2 can be performed at high speed and highly efficiently based on the 2-dimensional intensity distribution of the 2-dimensional transmitted waves 34 falling on the sheet of paper 2.

According to the above inspection device 80, the THz wave sensing unit 85 uses a plurality of THz wave detection devices 85*a*, 85*b*, 85*c*, 85*d* and a plurality of lenses 85*e*, but does not use an optical component such as a Fresnel lens, the downsizing can be achieved.

(Modification 3 of the Third Embodiment)

FIG. 13 (*a*) to FIG. 13 (*c*) are drawings describing an inspection device 90 according to modification 3 of the third embodiment of the present invention, where FIG. 13 (*a*) is a front view, FIG. 13 (*b*) is a right-side view, and FIG. 13 (*c*) is a rear view. This inspection device 90 is structured to detect the reflected waves 52 as in the case of the inspection device 50 shown in FIG. 9 (*a*) to FIG. 9 (*c*). The THz wave irradiation unit 93 has the same structure as that of the inspection device 50 shown in FIG. 9 (*a*) to FIG. 9 (*c*), but differs from the inspection device 50 shown in FIG. 9 (*a*) to FIG. 9 (*e*) in that the THz wave sensing unit 95 has a plurality of THz wave detection, devices 95*a*, 95*b*, 95*c*, 95*d*.

The THz wave sensing unit 95 is disposed on the upper side of the paper transfer unit 32 in order to detect the reflected waves 52, and at the position of reflected waves 52 to be scanned, a plurality of lenses 95*e* and Schottky barrier diodes, namely the plurality of THz wave detection devices 95*a*, 95*b*, 95*c*, 95*d*, are disposed.

According to this inspection device 90, a side of the sheet of paper 2 (X direction) is scanned by one THz wave oscillator 93*a*, and the THz waves reflected from the sheet of paper are detected by each Schottky diode, namely THz wave detection devices 95*a*, 95*b*, 95*c*, 95*d*. By transferring the sheet of paper 2 sequentially in the direction of the other side (Y), the non-contact detection of the foreign matter 7 adhering to the sheet of paper 2 can be performed at high speed and highly efficiently based on the 2-dimensional intensity distribution of reflected waves 52 from the sheet of paper.

According to the above inspection device 90, since the THz wave sensing unit 95 uses a plurality of THz wave detection devices 95*a*, 95*b*, 95*c*, 95*d*, and a plurality of lenses 95*e*, but does not use the optical components such as a Fresnel lens, the downsizing can be achieved.

The inspection device 90 is structured to detect reflected waves 52 from the surface of the sheet of paper 2. However, in order to detect the reflected waves from the back face of the sheet of paper 2, another THz wave irradiation unit 93 and another THz wave sensing unit 95 may be further provided on the lower side of the paper transfer unit 32.

(Modification 4 of the Third Embodiment)

Figure 14:
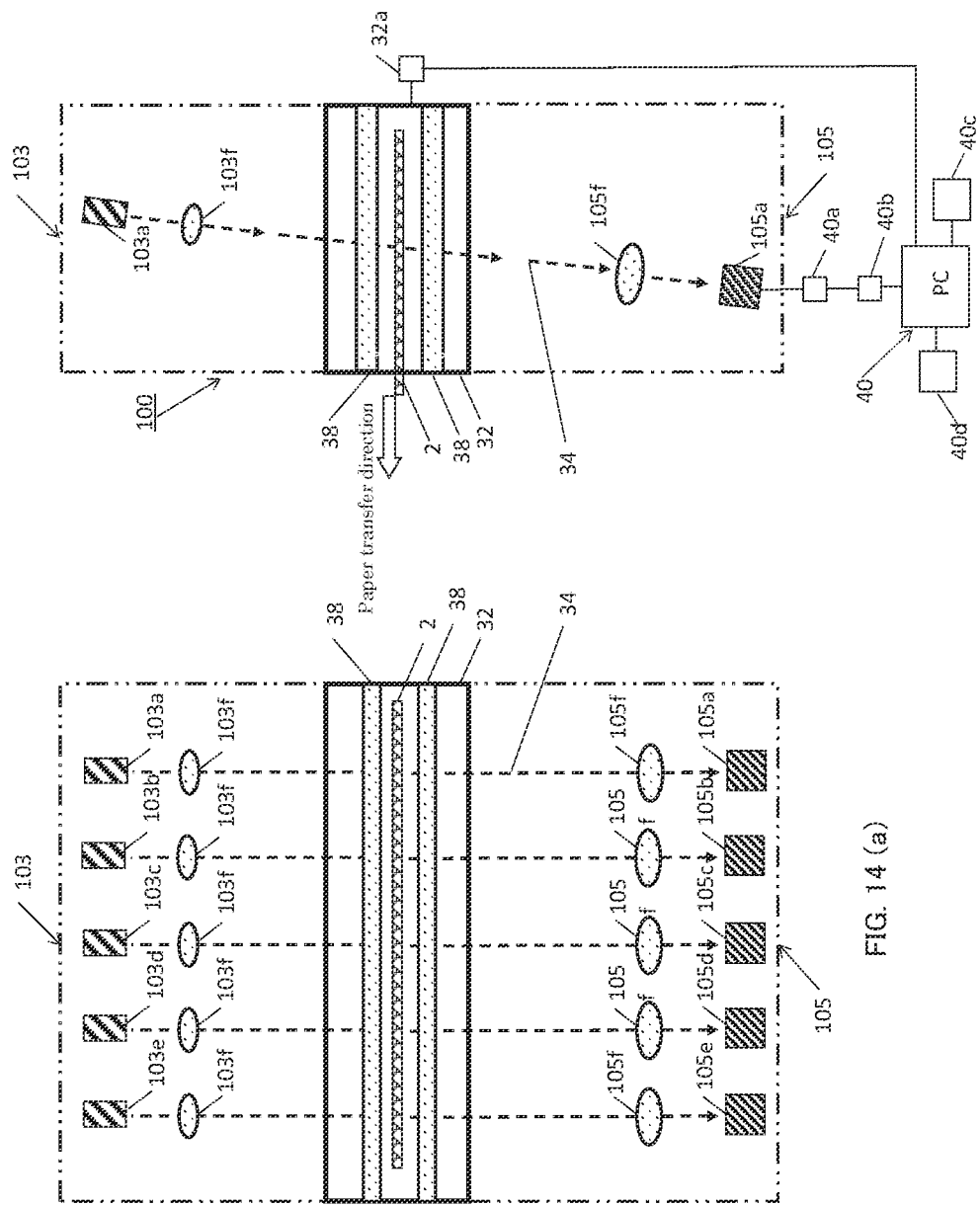
FIG. 14 (a) and FIG. 14 (b) are drawings describing an inspection device according to modification 4 of the third embodiment of the present invention, where FIG. 14 (a) is a front view, and FIG. 14 (b) is a right-side view.

FIG. 14 is a drawing FIG. 14 (*a*) and FIG. 14 (*b*) are drawings describing an inspection device 100 according to modification 4 of the third embodiment of the present invention, where FIG. 14 (*a*) is a front view, and FIG. 14 (*b*) is a right-side view. This inspection device 100 is structured to detect the transmitted waves 34 as in the case of the inspection device 30 shown in FIG. 8 (*a*) and FIG. 8 (*b*), and includes: a THz wave irradiation unit 103 made of a plurality of THz wave oscillators 103*a*, 103*b*, 103*c*, 103*d*, 103*e* disposed on the upper side of the paper transfer unit 32; and a THz wave sensing unit 105 made of a plurality of THz wave detectors 105*a*, 105*b*, 105*c*, 105*d*, 105*e*.

Specifically, as in the case of the inspection device 60 shown in FIG. 10 (*a*) and FIG. 10 (*b*), the THz wave irradiation unit 103 includes: a plurality of THz wave oscillators 103*a*, 103*b*, 103*c*, 103*d*, 103*e*; and a plurality of corresponding, lenses 103*f* disposed between the THz wave oscillators 103*a*, 103*b*, 103*c*, 103*d*, 103*e* and the paper transfer unit 32.

As in the case of the inspection device 80 shown in FIG. 12 (*a*) and FIG. 12 (*b*), in the THz wave sensing unit 105, a plurality of lenses 105*f* and the Schottky barrier diodes, namely a plurality of THz wave detection devices 105*a*, 105*b*, 105*c*, 105*d*, 105*e*, are disposed at positions in the width direction of the sheet of paper 2 (X direction in FIG. 2) where transmitted waves 34 are emitted.

The plurality of THz wave oscillators 103*a*, 103*b*, 103*c*, 103*d*, 103*e* may be controlled by the information processing unit 40 so as to generate pulses in a specified order in the width direction of the sheet of paper 2 (X direction in FIG. 2). For example, the THz wave oscillators 103*a*, 103*b*, 103*c*, 103*d*, 103*e* are made to generate pulses in that order, the sheet of paper 2 is then transferred in the transfer direction (Y direction in FIG. 2) for a specified distance, and then the THz wave oscillators 103*a*, 103*b*, 103*c*, 103*d*, 103*e* are made to generate pulses sequentially again. By repeating this operation, the sheet of paper 2 can be 2-dimensionally scanned.

In the THz wave sensing unit 105, the transmitted waves 4 of the THz waves from each THz wave oscillator 103*a*, 103*b*, 103*c*, 103*d*, 103*e* disposed in the width direction of the sheet of paper 2 (X direction in FIG. 2) are made to fall on the corresponding THz wave detection devices 105*a*, 105*b*, 105*c*, 105*d*, 105*e*, and the 2-dimensional signal distribution of the transmitted waves 34 of the THz waves can be acquired by 2-dimensionally scanning the sheet of paper 2.

According to the above inspection device 100, the THz wave irradiation unit 103 includes: a plurality of THz wave oscillators 103*a*, 103*b*, 103*c*, 103*d*, 103*e*; and a plurality of lenses 103*f*, and does not include a scanning device, the downsizing can be achieved. Furthermore, since the scanning device having the driving part is not used, the reliability increases. Furthermore, since the THz wave sensing unit 105 includes the plurality of THz wave detectors 105*a*, 105*b*, 105*c*, 105*d*, 105*e*, and the plurality of lenses 105*f*, and does not include a light-collecting optical component, the downsizing can be achieved and at the same time the reliability increases.

(Modification 5 of the Third Embodiment)

Figure 15:
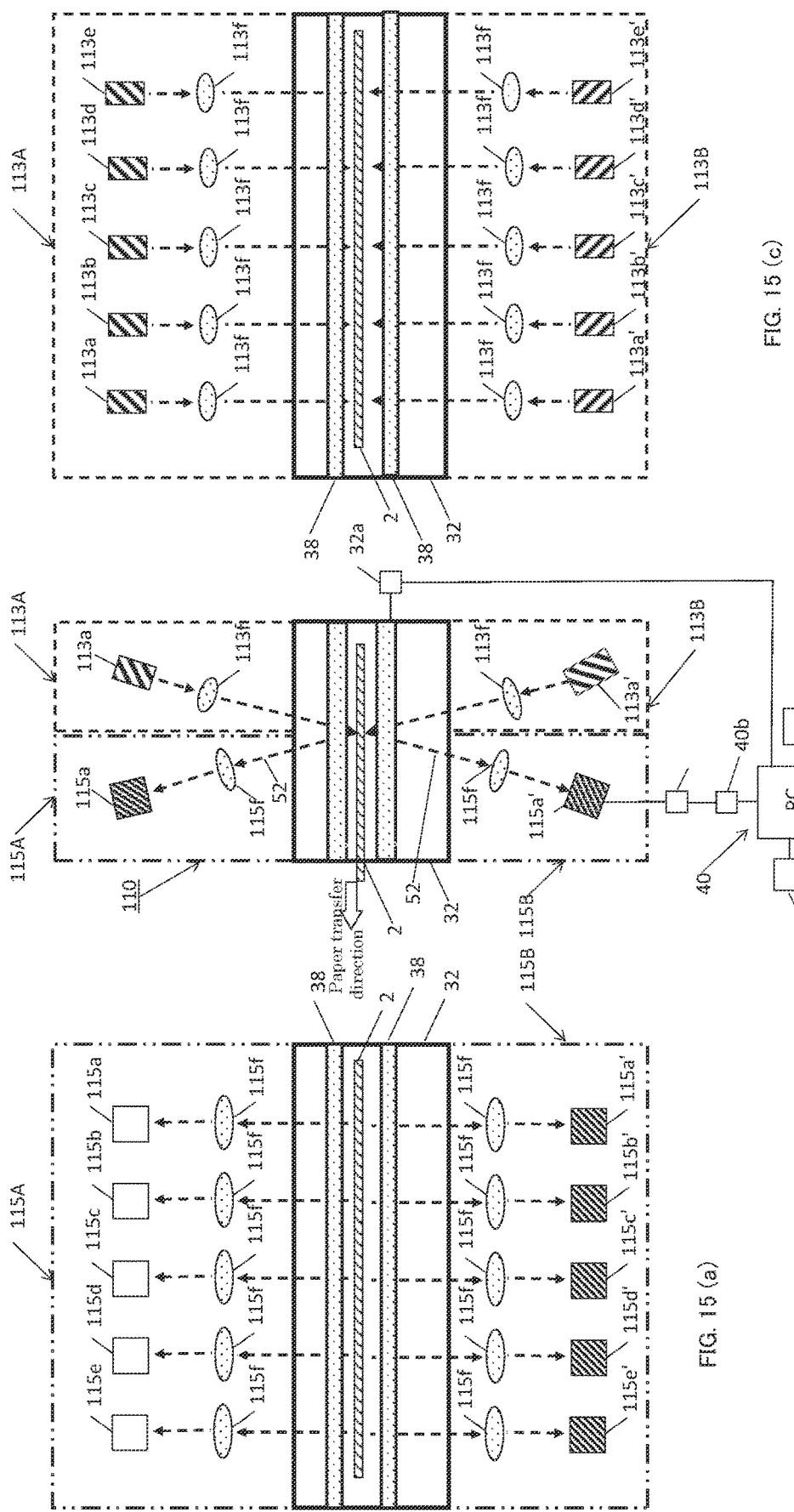
FIG. 15 (a) to FIG. 15 (c) are drawings describing an inspection device according to modification 5 of the third embodiment of the present invention, where FIG. 15 (a) is a front view, FIG. 15 (b) is a right-side view, and FIG. 15 (c) is a rear view.

FIG. 15 (*a*) to 15 (*c*) are drawings describing an inspection device 110 according to modification 5 of the third embodiment of the present invention, where FIG. 15 (a) is a front view, FIG. 15 (b) is a right-side view, and FIG. 15 (c) is a rear view. This inspection device 110 is structured to detect the reflected waves 52 as in the case of the inspection device 70 shown in FIG. 11 (a) to FIG. 11 (c), and includes: a first and a second THz wave irradiation units 113A, 113B; a first and a second. THz wave detection units 115A, 115B, etc. in order to inspect the front and the rear faces of the sheet of paper 2.

The first THz wave irradiation unit 113A has the same structure as the THz wave irradiation unit 73 shown in FIG. 11(a) to FIG. 11 (c) and includes: THz wave oscillators 113a, 113b, 113c, 113d, 113e; and a plurality of lenses 113f Similarly, the second THz wave irradiation unit 113E includes: THz wave oscillators 113a', 113b', 113c', 113d'. 113e' and a plurality of lenses 113f.

The first THz wave sensing unit 115A has the same structure as the THz wave sensing unit 105 shown in FIG. 14 (a), FIG. 14 (b) and includes: THz wave detection devices 115a, 115b, 115c, 115d, 115e: and a plurality of lenses 115f Similarly, the second THz wave sensing unit 115B includes: THz wave detection devices 115a', 115b', 115c', 115d', 115e'; and a plurality of lenses 115f.

In order to inspect the front and the rear faces of the sheet of paper 2, the control unit 40 controls the first and the second THz wave irradiation units 113A, 113B, and the irradiation timing signals from the first and the second THz wave irradiation units 113A, 113B are input.

Assuming the top face of the sheet of paper 2 to be the front face, THz waves emitted from the first THz wave irradiation unit 113A and reflected from the surface of the sheet of paper 2 are detected by the first THz wave sensing unit 115A.

Specifically, the foreign matter 7 on the surface of the sheet of paper 2 is detected as follows: the THz waves emitted from the first THz wave irradiation unit 113A and the reflected THz waves from the surface of the sheet of paper 2 are detected by the first THz wave sensing unit 115A, and the 2-dimensional intensity distribution of the reflected waves 52 in the THz band is acquired by the control unit 40.

THz waves are emitted from the second THz wave irradiation unit 113B disposed on the lower side of the paper transfer unit 32. The THz waves reflected from the back face of the sheet of paper 2 are detected by the second THz wave sensing unit 115B. Specifically, the foreign matter 7 on the back face of the sheet of paper 2 is detected as follows: the THz waves emitted from the second THz wave irradiation unit 113B and the reflected THz waves from the back face of the sheet of paper 2 are detected by the second THz wave sensing unit 115B, and the 2-dimensional intensity distribution of the reflected waves 52 in the THz band is acquired by the control unit 40.

According to this inspection device 110, the foreign matter 7 adhering to the front and the back faces of the sheet of paper 2 can be detected.

Irradiation and detection are repeated in a specified order as follows: the irradiation of THz waves by the first THz wave irradiation unit 113A; the detection of reflected THz waves by the first THz wave sensing unit 115A; the irradiation of THz waves by the second THz wave irradiation unit 113B; and the detection of reflected THz waves by the second THz wave sensing unit 115B.

According to the above inspection device 110, since the first and the second THz wave irradiation units 113A, 113B and the first and the second THz wave sensing units 115A, 115B do not include a scanning device, the downsizing is achieved. At the same time, since the scanning device having the driving part is not used, the reliability increases.

More detailed description of the present invention will be provided below by referring to examples, but the present invention is not limited to those examples only.

EXAMPLE 1

(Effect of Gradation on the Detection of Transmitted Waves)

The effect of gradation on the 2-dimensional intensity distribution will be described by referring to the inspection device 1 using 90 GHz transmitted waves 4, which was described by referring to FIGS. 2 and 3.

Figure 16:
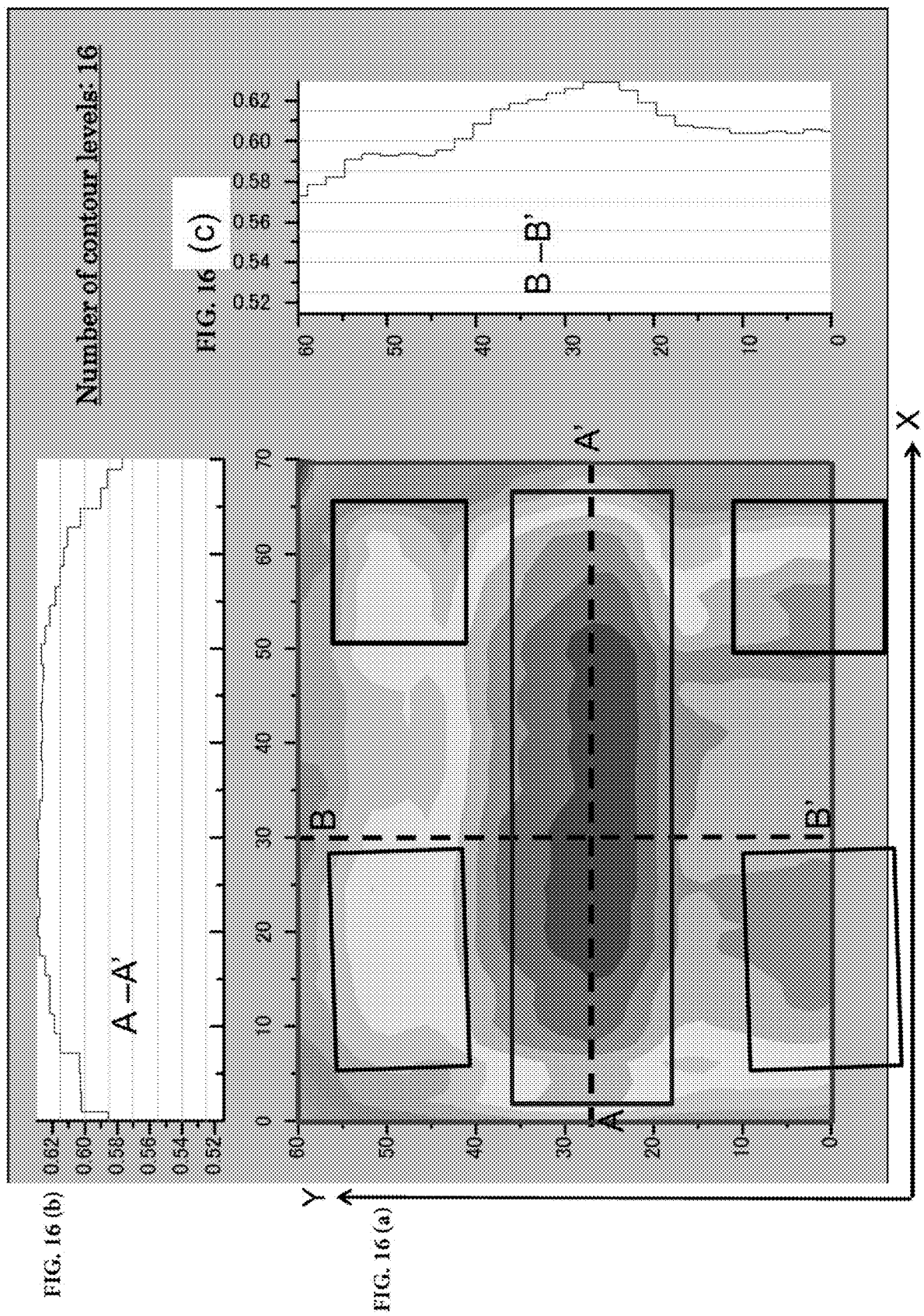
FIG. 16 (a) to FIG. 16 (c) are charts showing the number of contour levels 16 of 2-dimensional intensity distribution of 90 GHz waves having transmitted a Singapore dollar bill obtained by using an inspection device using 90 GHz transmitted waves, where FIG. 16 (a) is 2-dimensional intensity distribution, FIG. 16 (b) is the intensity distribution in a direction along A-A' in FIG. 16 (a), and FIG. 16 (c) is the intensity distribution in a direction along B-B' in FIG. 16 (a).

FIG. 16 (a) to FIG. 16 (c) are charts showing the number of contour levels 16 in 2-dimensional intensity distribution of 90 GHz waves having passed the Singapore dollar bill 2a obtained with the inspection device 1 using 90 GHz transmitted waves 4, where FIG. 16 (a) is the 2-dimensional intensity distribution, FIG. 16 (b) is the intensity distribution in a direction along A-A' in FIG. 16 (a), and FIG. 16 (c) is the intensity distribution in a direction along B-B' in FIG. 16 (a). The conditions of irradiating the Singapore dollar bill 2a with THz waves are the same as the case shown in FIG. 2: by using 90 GHz waves, the difference in intensity of transmitted waves 4 between a case where the Singapore dollar bill only was used and a case where the mending tape 7a was attached to the Singapore dollar bill 2a was obtained as the 2-dimensional intensity distribution of THz waves.

The intensity distribution in the direction along A-A' shown in FIG. 16(b) is the intensity distribution in the width direction (X direction) of the Singapore dollar bill 2a, showing that at the part to which the mending tape 7a is attached, the intensity of transmitted waves 4a is high. Since the number of contour levels is 16 in the 2-dimensional intensity distribution of THz waves, the intensity distribution of transmitted waves 4a within the mending tape 7a can also be determined.

The intensity distribution in a direction along B-B' shown in FIG. 16(c) is the intensity distribution on the mending tape 7a in a direction orthogonal to the width direction of the Singapore dollar bill 2a (Y direction), showing that at the part of the Singapore dollar bill 2a to which the mending tape 7a is attached, the intensity of the transmitted waves 4a is high, and that at the part of the Singapore dollar bill 2a to which the mending tape 7a is not attached, the intensity of transmitted waves 4a is low.

Figure 17:
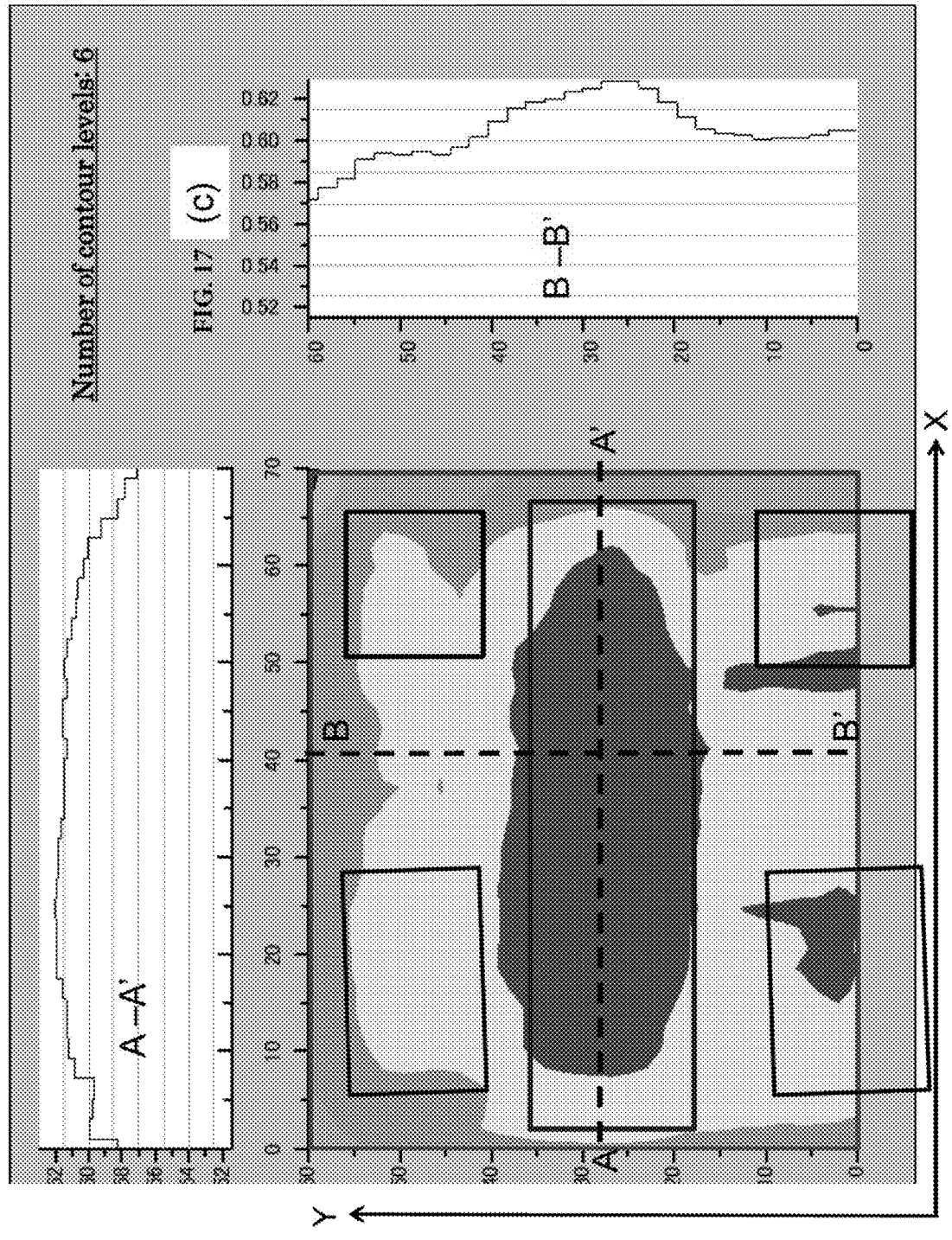
FIG. 17 (a) to FIG. 17 (c) are charts showing the number of contour levels 6 of 2-dimensional intensity distribution of 90 GHz waves having transmitted a Singapore dollar bill obtained by an inspection device using 90 GHz transmitted waves, where FIG. 17 (a) is 2-dimensional intensity distribution, FIG. 17 (b) is the intensity distribution in a direction along A-A' in FIG. 17 (a), and FIG. 17 (c) is the intensity distribution in a direction along B-B' in FIG. 17 (a).

FIG. 17 (a) to FIG. 17 (c) are charts showing the number of contour levels 6 of the 90 GHz waves having passed the Singapore dollar bill 2a obtained with the inspection device 1 using the 90 GHz transmitted wave 4, where FIG. 17 (a) is the 2-dimensional intensity distribution, FIG. 17 (b) is the intensity distribution in a direction along A-A', and FIG. 17 (c) is the intensity distribution in a direction along B-B'.

As shown in this chart, since the number of contour levels is 6 in the 90 GHz 2-dimensional intensity distribution, the position of the mending tape 7a can be determined at a glance. To judge whether the foreign matter 7 such as the mending tape 7a exists on the Singapore dollar bill 2a, the number of contour levels of 6 is thus proven to be sufficient as shown in FIG. 17(a) to FIG. 17 (c).

Intensity of Transmitted Waves Obtained When the Angle of Incidence is Changed from 0° to 35°

The intensity of the transmitted waves 4 was measured by changing the angle of incidence (θ) into the sheet of paper from 0° to 35° at 90 GHz.

Figure 18:
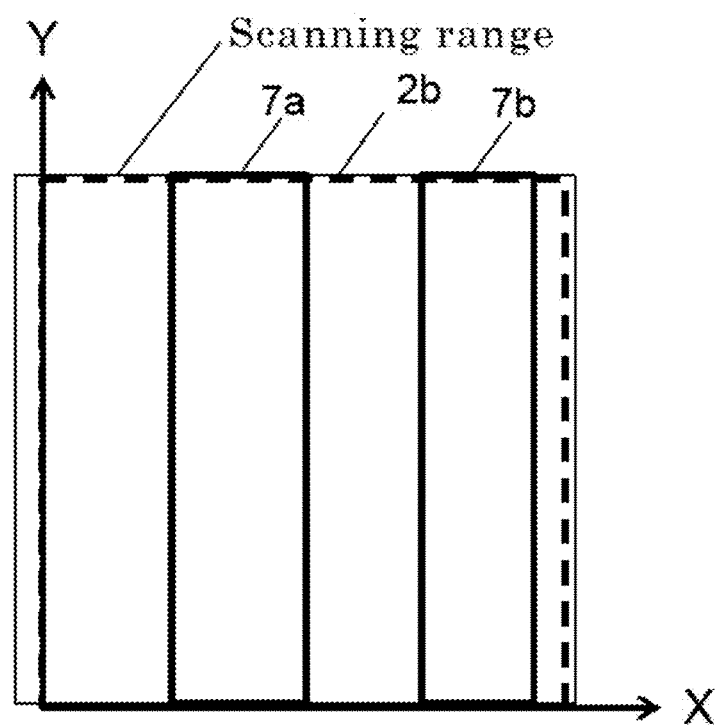
FIG. 18 is a chart describing a position of attaching a tape on copy paper (attachment in Y direction).

FIG. 18 is a chart describing the position of attaching tape to a copy paper (attachment in Y direction). As shown in this chart, the copy paper 2b was used as the sheet of paper 2, and an 18 mm-wide mending tape 7a and a 10 mm-wide cellophane tape 7b were attached in a longitudinal direction (Y direction) of the copy paper 2b. As in the case of the measurement of 90 GHz transmitted waves described by referring to FIGS. 1, 2, and 3, the 2-dimensional intensity of the transmitted waves was measured by changing the angle of incidence from 0° to 35°.

FIG. 19 (a) to FIG. 19 (d) are charts showing the 2-dimensional intensity of transmitted waves obtained by attaching the mending tape and the cellophane tape in parallel to the copy paper, as shown in FIG. 18, and changing the angle of incidence of the 90 GHz transmitted waves, where FIG. 19 (a) shows the intensity when the angle of incidence is 0° and 5°, FIG. 19 (b) shows the intensity when the angle of incidence is 10° and 15°, FIG. 19 (c) shows the intensity when the angle of incidence is 20° and 25°, and FIG. 19 (d) shows the intensity when the angle of incidence is 30° and 35°. The coordinate describing the angle of incidence of 10° to 35° is the same as the coordinate describing the angle of incidence of 0°. In the chart, the intensity of transmitted waves is high at black part, whereas that is low at white part.

As apparent from FIG. 19 (a) to FIG. 19 (d), when the angle of incidence is 0° (vertical incidence) and 5°, the intensity of transmitted waves from the mending tape 7a and the cellophane tape 7b is low, making judgment difficult. Meanwhile, when the angle of incidence is 10° or more, the intensity of the transmitted waves from the mending tape 7a and the cellophane tape 7b increases, thereby showing at a glance that these tapes have been attached.

As described above, when the angle of incidence is vertical or near vertical, a cyclic transmission intensity pattern appears due to interference between the reflected waves and incident waves into the sheet of paper 2, which inhibits the identification of the attached object 7 and is undesirable. Based on the result as shown in FIG. 19 (a) to FIG. 19 (d), the angle of incidence (θ) of approximately 10° or larger is desirable.

Relation Between the Angle of Incidence and the Intensity of Transmitted Waves

The intensity of transmitted waves 4 was measured by changing the angle of incidence (θ) of 90 GHz THz waves into a sheet of paper.

Figure 20:
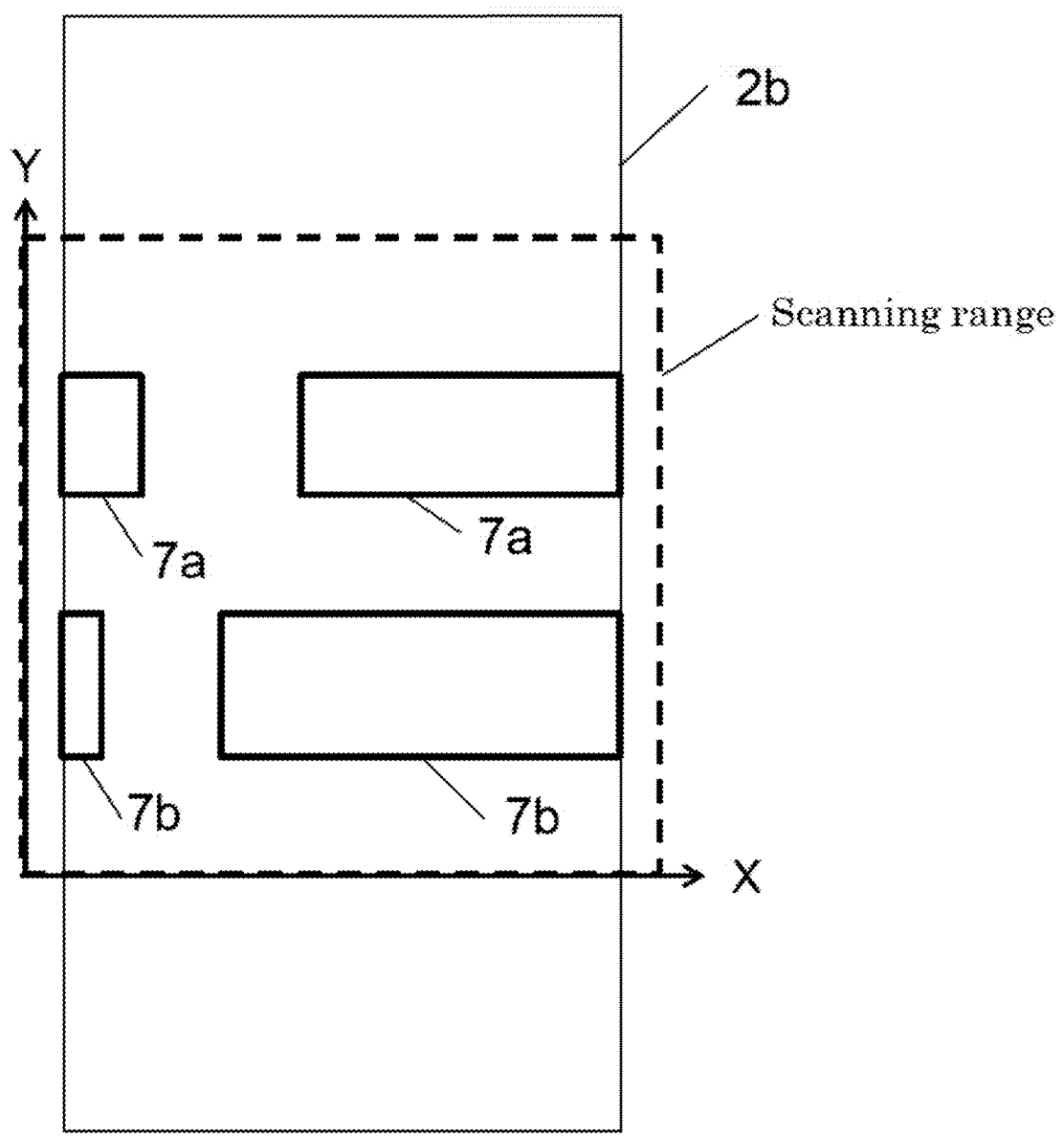
FIG. 20 is a chart describing the position of attaching tapes to copy paper (attachment in X direction).

FIG. 20 is a chart describing the position of attaching tape to the copy paper 2b (attachment in X direction). As shown in FIG. 20, the copy paper 2b was used as the sheet of paper 2, and on both faces of the sheet, 40 mm×15 mm and 10 mm×15 mm cellophane tape 7a and 50 mm×18 mm and 5 mm×18 mm mending tape 7b were attached in parallel in X direction.

Figure 21:
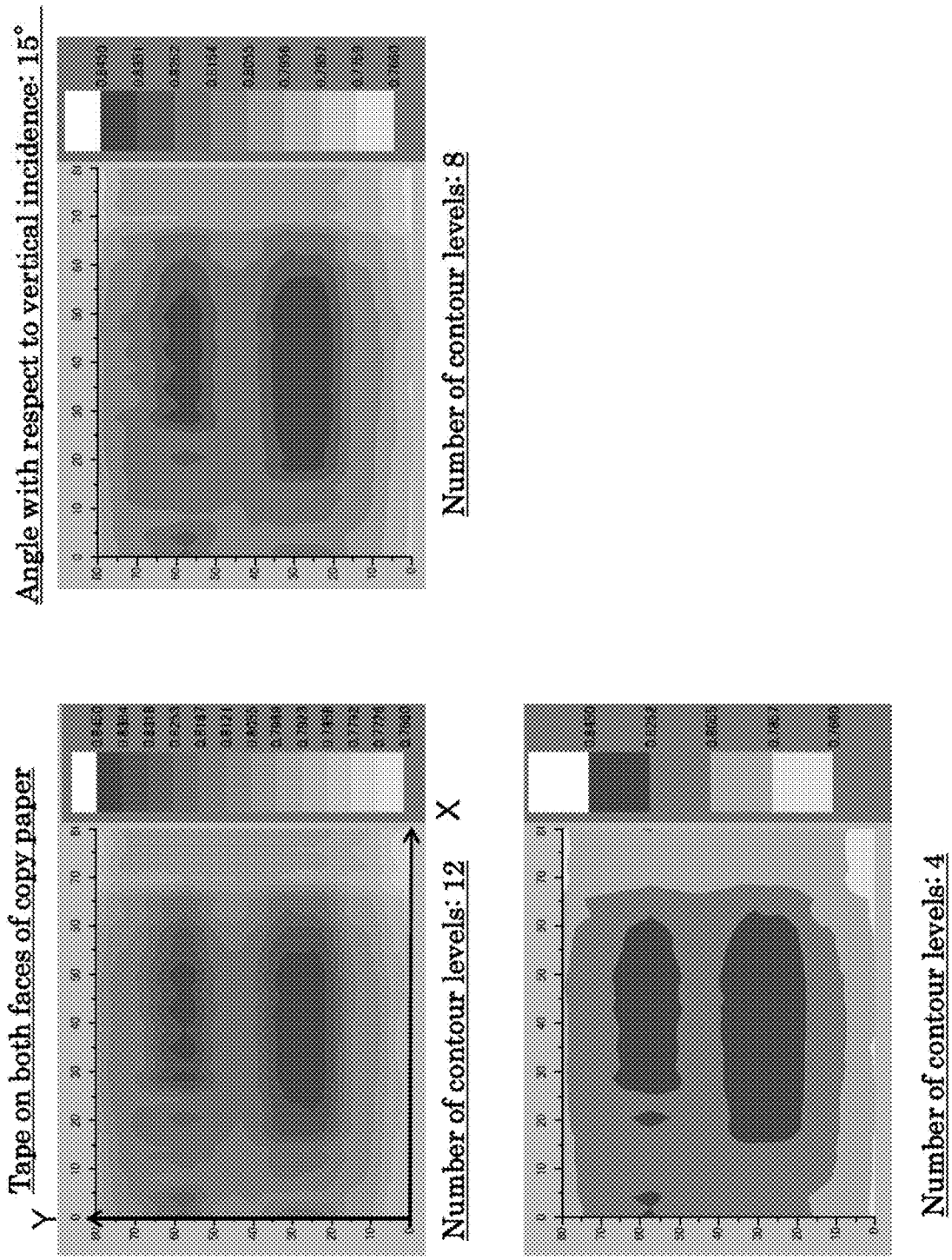
FIG. 21 is a chart Showing 2-dimensional intensity distribution of 90 GHz waves having transmitted the copy paper shown in FIG. 20 and been polarized in Y direction at the angle of incidence of 15°.

FIG. 21 is a chart showing the 2-dimensional intensity distribution of 90 GHz waves having transmitted the copy paper 2b shown in FIG. 20 and been polarized in Y direction at the angle of incidence of 15°. The conditions of irradiating the copy paper 2b with THz waves are the same as the case shown in FIG. 1: by using 90 GHz waves, the difference in intensity between a case where the copy paper 2b only was used and a case where the tape was attached to the copy paper 2b was obtained as 2-dimensional intensity distribution of THz waves. The orientation of waveguide of an oscillator 3a using a Gunn diode and that of the Schottky barrier diode 5c were set so that the same polarization direction is obtained. As the waveguide of the oscillator 3a using the Gunn diode and that of the Schottky barrier diode 5c, a waveguide and a horn antenna connected to the waveguide were used.

As shown in FIG. 21, with the 2-dimensional intensity distribution of THz waves at the angle of incidence of 15°, the existence of the tape adhering to the copy paper 2b can be identified clearly in any of the cases where the number of contour levels is 12, 8, and 4. The coordinate in FIG. 21 describing the number of contour levels of 8 and 4 is the same as the coordinate describing the number of contour levels of 12. The same applies to other figures unless otherwise designated.

FIG. 22 is a chart showing the 2-dimensional intensity distribution of 90 GHz waves having transmitted the copy paper 2b shown in FIG. 20 and been polarized in Y direction at the angle of incidence of 45°. The measurement conditions are the same as those of the case shown in FIG. 21 except that the angle of incidence is 45°. As shown in this figure, with the 90 GHz 2-dimensional intensity distribution when the angle of incidence is 45°, the existence of the tape adhering to the copy paper 2b can be identified clearly in any of the cases where the number of contour levels is 12, 8, and 4.

The 90 GHz 2-dimensional intensity distributions obtained in FIGS. 21 and 22 change by varying the angle of incidence from 15° to 45°, and it was found that the existence of the tape adhering to the copy paper 2b can be identified clearly even when the number of contour levels is 4.

Effect of Polarization

The intensity of transmitted waves was measured by changing polarization when irradiating the sheet of paper 2 with THz waves.

The position of copy paper 2b to which a tape was attached was the same as FIG. 20, and the 2-dimensional intensity distribution of THz waves having transmitted the copy paper 2b was measured in the same manner as FIG. 21 except that the polarization direction was shifted from that of the case shown in FIG. 21 by 90° (to vertical direction) so that X-direction polarization to occur.

FIG. 23 is a chart showing the 2-dimensional intensity distribution of THz waves having transmitted the copy paper 2b shown in FIG. 20 and been polarized in X direction at the angle of incidence of 15°. As shown in this chart, with the 2-dimensional intensity distribution of THz waves when the angle of incidence is 15°, the existence of the tape adhering to the copy paper 2b can be identified in any of the cases where the number of contour levels is 12, 8, and 4, but the identification was found to be more difficult than FIG. 21. In other words, the 2-dimensional intensity distribution of THz waves different from that in FIG. 22 was obtained. It was thus found that the 2-dimensional intensity distribution of THz waves transmitting the copy paper 2b changes by controlling the polarization direction of THz waves falling on the copy paper 2b.

FIG. 24 is a chart showing the 2-dimensional intensity distribution of THz waves having transmitted the copy paper 2b shown in FIG. 20 and been polarized in X direction at the angle of incidence of 45°. As shown in this figure, with the 2-dimensional intensity distribution of THz waves when the angle of incidence is 45°, the existence of the tape adhering to the copy paper 2b can be identified in any of the cases where the number of contour levels is 12, 8, and 4, but the identification was found to be more difficult than FIG. 22. In other words, the 2-dimensional intensity distribution of the THz waves different from that in FIG. 22 was obtained. It was thus found that the 2-dimensional intensity distribution of THz waves transmitting the copy paper 2b changes by controlling the polarization direction of THz waves falling on the copy paper 2b.

The 2-dimensional intensity distribution of the THz waves obtained in FIGS. 23 and 24 clearly differs from the data of polarization in Y direction as shown in FIGS. 21 and 22, and is found to change in accordance with the polarization direction of the THz waves falling on the copy paper 2b.

EXAMPLE 2

90 GHz Reflection Measurement

Example 2, where 90 GHz reflection measurement was performed, will be described.

As the THz wave oscillator 3a, 90 GHz continuous oscillating (CW oscillation) Gunn diode oscillator was used to allow the waves to fall on the sheet of paper 2 at an angle of 45° with respect to the vertical direction of the paper, and reflected waves 22 were measured. The orientation of the wave guide of oscillator 3a using the Gunn diode and that of the Schottky barrier diode 5c were set so as to ensure the same polarization direction as shown in FIG. 23.

FIG. 25 is a chart showing the 2-dimensional intensity distribution of 90 GHz waves having been reflected from the copy paper 2b shown in FIG. 18 and polarized in X direction at the angle of incidence of 45°. The position of attaching the tape was the same as FIG. 18. As shown in FIG. 18, the copy paper 2b was used as the sheet of paper 2, and on both faces of the sheet of paper, 10 mm×70 mm cellophane tape 7b and 18 mm×70 mm mending tape 7a are attached. In the scanning range of 70 mm (X direction)×70 mm (Y direction), the intensity distribution of reflected waves 22 was measured at every 2 mm.

As shown in FIG. 25, with the 2-dimensional intensity distribution of reflected waves 22 of 90 GHz waves when the angle of incidence was 45°, the intensity of reflected waves 22 of the 90 GHz waves from the tape was lower than the intensity of reflected waves 22 from the copy paper 2b in any of the cases where the number of contour levels is 12, 8, and 4. The existence of the tape adhering to the copy paper 2b was identified, but unlike the case of 60 GHz waves, the intensity of reflection from the tape was found to be lower than the intensity of reflection from the copy paper 2b.

EXAMPLE 3

140 GHz Transmission Measurement

Next, Example 3, where 140 GHz transmission measurement was performed, will be described.

As the THz wave oscillator 3a, an oscillator using 140 GHz continuous oscillation (CW oscillation) IMPATT diode (ELVA-1, model CIDO-06/140/20) was used to allow waves to fall on the sheet of paper 2 at an angle of 15° with respect to the vertical direction of the paper 2 and transmitted waves 4 were measured. The output was approximately 10 mW. The orientation of the waveguide of the oscillator 3a using the IMPATT diode and that of the Schottky barrier diode 5c (ELVA-1, model ZGD-06) were set so as to ensure the same polarization direction as shown in FIG. 21. Other conditions were the same as the measurement of 90 GHz transmitted waves 4.

The high-quality paper was used as the sheet of paper 2, and on its both sides, 10 mm×70 mm cellophane tape 7b and 18 mm×70 mm mending tape 7a were attached at the same positions as FIG. 18 so that their longitudinal direction becomes Y direction. Within the scanning range of 70 mm (X direction)×70 mm (Y direction), the intensity distribution of the transmitted waves 4a was measured at every 2 mm.

FIG. 26 is a chart showing the 2-dimensional intensity distribution of 140 GHz waves having transmitted the high-quality paper to which the tape as shown in FIG. 18 was attached and been polarized in Y direction at the angle of incidence of 15°. In the coordinate shown in FIG. 16 (a) to FIG. 16(c), the top-bottom direction on the paper is X direction, and left-right direction on the paper is Y direction.

As shown in FIG. 26, with the 2-dimensional intensity distribution of the transmitted waves 4a of 140 GHz waves when the angle of incidence was 15°, unlike the case of 90 GHz where transmitted waves 4a from the tape was higher than the intensity of transmitted waves 4a from the copy paper 2b, the intensity of 140 GHz transmitted waves 4a from the tape was lower than the intensity of transmitted waves 4 from the high-quality paper in any of the cases where the number of contour levels was 12, 8, and 4. When the number of contour levels was 4, the position of the cellophane tape 7b and the mending tape 7a having been attached in Y direction can be identified clearly. Existence of the tape adhering to the high-quality paper can be identified clearly, but unlike the case of 90 GHz, the intensity of the transmitted waves from the tape was found to be lower than, the intensity of transmitted waves from the high-quality paper.

From the result as shown in FIG. 26, the relation between the intensity of transmitted waves from the copy paper or the high-quality paper and the intensity of transmitted waves from the tape adhering to the copy paper or the high-quality paper was found to change by changing the frequency of the THz waves emitted to the copy paper or the high-quality paper, but the existence of the tape was also found to be clearly identifiable.

EXAMPLE 4

140 GHz Reflection Measurement

Example 4, where 140 GHz reflection measurement was performed, will be described.

The reflection measurement at 140 GHz was performed in the same manner as Example 2 where 90 GHz reflection was studied except that waves were made to fall on the sheet of paper 2 at an angle of 45° with respect to the vertical direction of the paper to measure the reflected waves 22.

The orientation of the waveguide of the oscillator 3a using IMPATT diode and that of the Schottky barrier diode 5c are set so as to ensure the same polarization direction as the measurement of transmitted waves as shown in FIG. 21. As shown in FIG. 18, on both sides of the high-quality paper, 10 mm×70 mm cellophane tape 7b and 18 mm×70 mm mending tape 7a were attached. In the scanning range of 70 mm (X direction)×70 mm (Y direction), the intensity distribution of reflected waves 22 was measured at every 2 mm.

Figure 27:
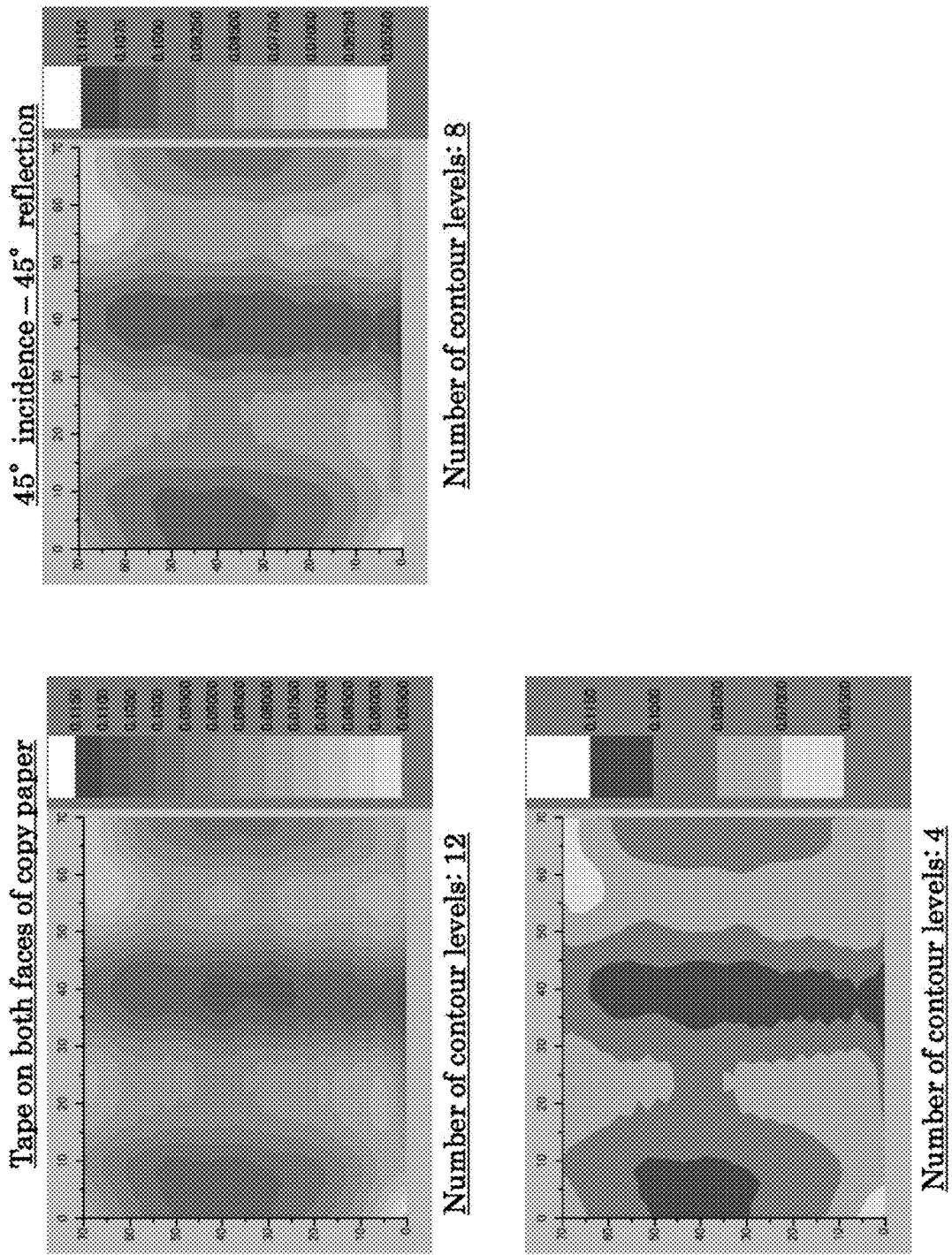
FIG. 27 is a chart showing 2-dimensional intensity distribution of 140 GHz waves having been reflected from the high-quality paper shown in FIG. 18 and polarized in Y direction at the angle of incidence of 45°

FIG. 27 is a chart showing the 2-dimensional intensity distribution of 140 GHz waves reflected from high-quality paper. As shown by this chart, with the 2-dimensional intensity distribution of the reflected waves 22 of the 140 GHz waves when the angle of incidence was 45°, unlike the case of 60 GHz where the intensity of reflected waves 22 from the tape was higher than the intensity of reflected waves 22 from the copy paper 2b, the intensity of the reflected waves 22 of the 140 GHz waves from the tape was lower than the intensity of reflected waves 22 from the high-quality paper 2b in any of the cases where the number of contour levels was 12, 8, and 4. The existence of the cellophane tape 7b and the mending tape 7a adhering to the high-quality paper was identified clearly, but the intensity of reflection from these tapes was found to be lower than the intensity of reflection from the high-quality paper unlike the case of 60 GHz.

Reflection measurement was performed by turning the polarization of the oscillator 3a using IMPATT diode and the Schottky barrier diode 5c by 90°. In this case, data similar to the 2-dimensional intensity distribution of reflected waves 22 shown in FIG. 27 was obtained.

From the result shown in FIG. 27, the relation between the intensity of reflected waves from the copy paper or the high-quality paper and the intensity of reflected waves from the tape adhering to the copy paper or the high-quality paper was found to change by changing the frequency of the THz waves emitted to the copy paper or the high-quality paper, but the existence of the tape was also found to be clearly identifiable.

The present invention is not limited to the examples described above, but can be modified variously within the scope of the claims, and needless to say, these modifications are included in the scope of the present invention.

REFERENCE SIGNS LIST

1: Inspection device according to a first embodiment
2: Specimen
2a: Singapore dollar bill
2b: Copy paper
3, 33, 63, 73, 83, 93, 103, 113: THz wave irradiation unit
3a, 33a, 63a-63d, 73a-73d, 83a, 93a, 103a-103e, 113a-113e, 113a'-113e': THz wave oscillator
3c, 33c: THz wave emitted from THz wave oscillator
3e, 35a, 55a, 65a, 75a: Light-collecting optical component
3f: Collected THz wave
4, 34: Transmitted wave
4a: Transmitted wave
5, 35, 55, 65, 75, 85, 95, 105, 115: THz wave sensing unit
5a: Lens
5c, 35c, 55c, 65c, 75c, 85a-85d, 95a-95d, 105a-105e, 115a-115e: THz wave detection device
7: Foreign matter
7a: Mending tape
7b: Cellophane tape
8: Resin film
8a: First optical resin film
8b: Second optical resin film
10, 40: Information processing unit
10a, 40a: A/D converter
10b, 40b: Input/output interface (I/O)
10c, 40c: Display
10d, 40d: Memory device
12: First medium
13: Second medium
14: Third medium
15: Fourth medium
16: Fifth medium
17: Sixth medium
18: Seventh medium
20: Another inspection device according to the first embodiment
22, 52: Reflected wave
30, 50: Inspection device according to a second embodiment
32: Paper transfer unit
32a: Control circuit
33d, 83d, 93d: Scanning device
33e, 63e, 73e, 83e, 93e, 103f, 113f: Lens
33f, 83f, 93f: Fresnel lens
33s: THz wave scanned by canning device
35b, 65b, 75b, 85e, 95e, 105f, 115f: Lens
60, 70, 80, 90, 100, 110: Inspection device according to the second embodiment
38: Glass

What is claimed is:
1. An inspection device, comprising:
a step motor or a belt and a motor configured to transfer a sheet of paper;
a THz wave irradiation unit comprising a scanning device, a THz wave oscillator configured to irradiate the sheet of paper with THz waves, the THz wave oscillator being configured to oscillate the THz waves and emit the oscillated THz waves to the sheet of paper via a first light-collecting optical component, and the scanning device being configured to scan the THz waves across the sheet of paper in a direction orthogonal to a transfer direction of the step motor or the belt and the motor, and the first light-collecting optical component inserted between the scanning device and the sheet of paper;
a THz wave sensing unit having a THz wave detection device configured to detect the transmitted waves or the reflected waves of the THz waves emitted to the sheet of paper; and
a processor configured to acquire a 2-dimensional intensity distribution of the transmitted waves or the reflected waves of the sheet of paper,
wherein the THz wave oscillator is configured to emit the THz waves to the sheet of paper via the first light-collecting optical component at an angle of incidence, which is set from several to 50 degrees, with respect to the thickness direction of the sheet of paper not to cause interference,
wherein the processor is configured to control the step motor or the belt and the motor to transfer the sheet of paper to the transfer direction,
and the processor is configured to detect whether or not a foreign matter is adhering to the sheet of paper at the time of inspection by comparing the intensity distribution obtained when the sheet of paper without attachment of the foreign matter is detected and the intensity distribution obtained when the sheet of paper is detected at the time of inspection.

2. The inspection device as set forth in claim 1, wherein the scanning device is any one of galvanometer mirror, polygon mirror, and digital mirror devices.

3. The inspection device as set forth in claim 1, wherein the THz wave sensing unit comprises: a THz wave detector in the THz wave detection device; and a second light-collecting optical component for collecting the transmitted waves or the reflected waves of the TH waves emitted to or the sheet of paper.

4. The inspection device as set forth in claim 3, wherein the second light-collecting optical component is selected from a Fresnel lens, convex lens, concave lens and mirror.

5. The inspection device as set forth in claim 1, wherein the THz wave sensing unit further comprises: a plurality of THz wave detectors in the THz wave detection device; and optical components inserted between the sheet of paper and each of the plurality of THz wave detectors, and
wherein the transmitted waves or the reflected waves in the direction orthogonal to the direction of transfer are collecting by the optical components and are detected by the plurality of the THz wave detectors.

6. The inspection device as set forth in claim 1, wherein a resin or glass is disposed on a top face and a bottom face of the sheet of paper.

7. The inspection device as set forth in claim 1, wherein the THz wave oscillator in the THz wave irradiation unit is a multiple-frequency THz wave oscillator.

8. The inspection device as set forth in claim 1, wherein the inspection device is configured to control a polarization direction of THz waves emitted from the THz wave irradiation unit and a polarization direction of THz waves falling on the THz wave detection device.

9. The inspection device as set forth in claim 1, the THz wave sensing unit further comprises: a second light-collecting optical component and a lens inserted between the sheet of paper and the THz wave detection device, and the second light-collecting optical component of the THz wave sensing unit has a function of collecting the transmitted waves or the reflected waves to the lens, and the collected transmitted waves or reflected waves by the lens are detected by the THz wave detection device.

10. An inspection device, comprising:
a step motor or a belt and a motor configured to transfer a sheet of paper;
a THz wave irradiation unit comprising:
　a THz wave oscillator configured to irradiate the sheet of paper with THz waves;
　a lens inserted between the THz wave oscillator and the sheet of paper, the THz wave oscillators being configured to oscillate the THz waves; and
　a scanning device configured to scan the THz waves across the sheet of paper in a direction orthogonal to a transfer direction of the step motor or the belt and the motor;
a THz wave sensing unit comprising:
　a plurality of THz wave detection devices configured to detect the transmitted waves or the reflected waves of the THz waves emitted to the sheet of paper; and
　a processor configured to acquire a 2-dimensional intensity distribution of the transmitted waves or the reflected waves of the sheet of paper,
wherein the lens of the THz wave irradiation unit is configured to emit the THz waves to the sheet of paper at an angle of incidence, which is set from several to 50 degrees, with respect to the thickness direction of the sheet of paper not to cause interference,
wherein the processor is configured to control the step motor or the belt and the motor to transfer the sheet of paper to the transfer direction,
and the processor is configured to detect whether or not a foreign matter is adhering to the sheet of paper at the time of inspection by comparing the intensity distribution obtained when the sheet of paper without attachment of the foreign matter is detected and the intensity distribution obtained when the sheet of paper is detected at the time of inspection.

11. The inspection device as set forth in claim 10, a resin or glass is disposed on a top face and a bottom face of the sheet of paper.

12. The inspection device as set forth in claim 10, wherein the THz wave oscillator in the THz wave irradiation unit is a multiple-frequency THz wave oscillator.

13. The inspection device as set forth in claim 10, wherein the inspection device is configured to control a polarization direction of THz waves emitted from the THz wave irradiation unit and a polarization direction of THz waves falling on each of the plurality of THz wave detection devices.

* * * * *